United States Patent
Takenouchi

(10) Patent No.: US 11,910,994 B2
(45) Date of Patent: Feb. 27, 2024

(54) MEDICAL IMAGE PROCESSING APPARATUS, MEDICAL IMAGE PROCESSING METHOD, PROGRAM, DIAGNOSIS SUPPORTING APPARATUS, AND ENDOSCOPE SYSTEM

(71) Applicant: FUJIFILM Corporation, Tokyo (JP)

(72) Inventor: Seiya Takenouchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 467 days.

(21) Appl. No.: 17/204,904

(22) Filed: Mar. 17, 2021

(65) Prior Publication Data

US 2021/0201486 A1 Jul. 1, 2021

Related U.S. Application Data

(63) Continuation of application No. PCT/JP2019/037482, filed on Sep. 25, 2019.

(30) Foreign Application Priority Data

Sep. 28, 2018 (JP) .................................. 2018-185057

(51) Int. Cl.
*G06T 7/12* (2017.01)
*A61B 1/00* (2006.01)
(Continued)

(52) U.S. Cl.
CPC .... *A61B 1/000094* (2022.02); *A61B 1/00045* (2013.01); *G06T 7/0012* (2013.01); *G06V 10/25* (2022.01); *G06T 2207/10068* (2013.01)

(58) Field of Classification Search
CPC .......... A61B 1/000094; A61B 1/00045; A61B 1/0638; A61B 1/0005; G06T 7/0012; G06T 2207/10068; G06V 10/25
(Continued)

(56) References Cited

U.S. PATENT DOCUMENTS 10,891,743 B2   1/2021  Hirota
2011/0228994 A1*  9/2011  Tanaka .................. G06T 7/0012
                                                            382/128
(Continued)

FOREIGN PATENT DOCUMENTS

CN   102740757   10/2012
CN   104853666   8/2015
(Continued)

OTHER PUBLICATIONS

Office Action of Japan Counterpart Application, with English translation thereof, dated Jan. 20, 2023, pp. 1-6.
(Continued)

*Primary Examiner* — Charlotte M Baker
(74) *Attorney, Agent, or Firm* — JCIPRNET

(57) ABSTRACT

Provided are a medical image processing apparatus, a medical image processing method, a program, a diagnosis supporting apparatus, and an endoscope system that emphasize a region of interest in a medical image at an appropriate emphasis degree. The above problem is solved by a medical image processing apparatus including: an emphasis processing unit that emphasizes a region of interest included in a time-series medical image at a set emphasis degree; a total-time measuring unit that measures a total time during which the region of interest is emphasized; and an emphasis-degree setting unit that sets the emphasis degree to a relatively larger value as the total time is relatively longer.

23 Claims, 17 Drawing Sheets

(51) Int. Cl.
*G06T 7/00* (2017.01)
*G06V 10/25* (2022.01)

(58) Field of Classification Search
USPC .......................................................... 382/128
See application file for complete search history.

(56) References Cited

U.S. PATENT DOCUMENTS

| | | |
|---|---|---|
| 2011/0237882 A1 | 9/2011 | Saito |
| 2012/0274754 A1 | 11/2012 | Tsuruoka |
| 2015/0276602 A1 | 10/2015 | Ishihara |
| 2015/0320296 A1 | 11/2015 | Morita |
| 2018/0249900 A1 | 9/2018 | Imaizumi et al. |
| 2018/0350075 A1* | 12/2018 | Grimmer .................. G06T 7/40 |
| 2020/0058124 A1 | 2/2020 | Iwaki |

FOREIGN PATENT DOCUMENTS

| | | |
|---|---|---|
| CN | 105050473 | 11/2015 |
| CN | 108348145 | 7/2018 |
| JP | 2006255021 | 9/2006 |
| JP | 2010035756 | 2/2010 |
| WO | 2014091964 | 6/2014 |
| WO | 2017073337 | 5/2017 |
| WO | 2017081976 | 5/2017 |
| WO | 2017221353 | 12/2017 |
| WO | 2018198161 | 11/2018 |

OTHER PUBLICATIONS

"International Search Report (Form PCT/ISA/210) of PCT/JP2019/037482," dated Nov. 19, 2019, with English translation thereof, pp. 1-5.

"Written Opinion of the International Searching Authority (Form PCT/ISA/237) of PCT/ JP2019/037482," dated Nov. 19, 2019, with English translation thereof, pp. 1-9.

"Search Report of Europe Counterpart Application", dated Oct. 5, 2021, pp. 1-8.

Office Action of Japan Counterpart Application, with English translation thereof, dated Sep. 21, 2022, pp. 1-6.

"Office Action of China Counterpart Application", dated Sep. 23, 2023, with English translation thereof, p. 1- p. 17.

* cited by examiner

MEDICAL IMAGE PROCESSING APPARATUS, MEDICAL IMAGE PROCESSING METHOD, PROGRAM, DIAGNOSIS SUPPORTING APPARATUS, AND ENDOSCOPE SYSTEM

CROSS-REFERENCE TO RELATED APPLICATIONS

The present application is a Continuation of PCT International Application No. PCT/JP2019/037482 filed on Sep. 25, 2019 claiming priority under 35 U.S.C § 119(a) to Japanese Patent Application No. 2018-185057 filed on Sep. 28, 2018. Each of the above applications is hereby expressly incorporated by reference, in its entirety, into the present application.

BACKGROUND OF THE INVENTION

1. Field of the Invention

The present invention relates to a medical image processing apparatus, a medical image processing method, a program, a diagnosis supporting apparatus, and an endoscope system, and particularly to a technique for reporting a region of interest in a time-series medical image.

2. Description of the Related Art

In the medical field, in recent years, a supporting function for automatically detecting a region of interest such as a lesion from a medical image such as an endoscopic image captured by an endoscope is expected to lead to prevention of missing of a lesion.

In such a supporting function, as a method for reporting the automatically detected result to a user, emphasis display for superposing a detection result on the region of interest in the image is known.

WO2017/073337A discloses an endoscope system that detects a candidate lesion region based on a feature quantity of a photographic subject observation image and performs emphasis processing of the candidate lesion region.

SUMMARY OF THE INVENTION

The endoscope system according to WO2017/073337A ends the emphasis processing if it is determined that detection of the candidate lesion region is continued for a predetermined time.

However, ending the emphasis processing may be insufficient as the supporting function in some cases. For example, the endoscope is difficult to operate, and if the emphasis processing ends while the endoscope is made to remain at an appropriate portion where the user wishes to observe, the user cannot sufficiently recognize the region of interest in some cases.

In addition, if emphasis processing at a relatively large emphasis degree is performed at the time of detection of the region of interest, an in-image change is large from an image not subjected to the emphasis processing to an image subjected to the emphasis processing, which may interrupt image observation.

The present invention has been made in view of such circumstances, and an object is to provide a medical image processing apparatus, a medical image processing method, a program, a diagnosis supporting apparatus, and an endoscope system that emphasize a region of interest in a medical image at an appropriate emphasis degree.

In order to achieve the above object, a medical image processing apparatus according to an aspect is a medical image processing apparatus including: an emphasis processing unit that emphasizes a region of interest included in a time-series medical image at a set emphasis degree; a total-time measuring unit that measures a total time during which the region of interest is emphasized; and an emphasis-degree setting unit that sets the emphasis degree to a relatively larger value as the total time is relatively longer.

According to this aspect, the region of interest included in the time-series medical image is emphasized at the set emphasis degree, the total time during which the region of interest is emphasized is measured, and the emphasis degree is set to a relatively larger value as the total time is relatively longer, and thus, the region of interest in the medical image can be emphasized at an appropriate emphasis degree.

The medical image processing apparatus preferably further includes: an image acquiring unit that acquires the time-series medical image; and a region-of-interest detecting unit that detects the region of interest from the medical image. Thus, the region of interest can be detected from the acquired medical image.

The total-time measuring unit preferably measures the total time of each of a plurality of regions of interest, and the emphasis-degree setting unit preferably sets the emphasis degree of the region of interest in accordance with the total time of the region of interest. Thus, an appropriate emphasis degree can be set for each of the plurality of regions of interest.

The medical image processing apparatus preferably further includes: a feature quantity calculating unit that calculates a feature quantity of the region of interest; a region-of-interest storage unit that stores the feature quantity and the total time of the region of interest in association with each other; and an identical-region-of-interest determining unit that determines, from a similarity degree between a feature quantity of a first region of interest included in a first medical image and a feature quantity of a second region of interest emphasized in a second medical image preceding the first medical image in time series, the feature quantity being stored in the region-of-interest storage unit, whether the first region of interest is identical with the second region of interest, in which, if it is determined that the first region of interest is identical with the second region of interest, the total-time measuring unit preferably measures a total time of the first region of interest by taking over a total time of the second region of interest. Thus, it is possible to take over the emphasis degree of the second region of interest that is identical with the first region of interest, as the emphasis degree of the first region of interest.

If it is determined that the first region of interest is not identical with the second region of interest, the identical-region-of-interest determining unit preferably further determines, from a similarity degree between the feature quantity of the first region of interest and a feature quantity of a third region of interest emphasized in a third medical image preceding the second medical image in time series, the feature quantity being stored in the region-of-interest storage unit, whether the first region of interest is identical with the third region of interest, and, if it is determined that the first region of interest is identical with the third region of interest, the total-time measuring unit preferably measures the total time of the first region of interest by taking over a total time of the third region of interest. Thus, it is possible to take over the emphasis degree of the third region of interest that is identical with the first region of interest, as the emphasis degree of the first region of interest even in a case in which the region of interest identical with the first region of interest is not included in the second medical image.

If it is determined that the first region of interest is not identical with the second region of interest, the identical-region-of-interest determining unit preferably determines whether the first region of interest exists at a position within a predetermined area in the first medical image, and, if it is determined that the first region of interest exists at the position within the predetermined area, the total-time measuring unit preferably measures the total time of the first region of interest by taking over the total time of the second region of interest. Thus, it is possible to take over the emphasis degree of the second region of interest as the emphasis degree of the first region of interest even in a case in which, although the first region of interest and the second region of interest are different regions, the first region of interest exists at the position within the predetermined area.

The emphasis processing unit preferably superposes a figure indicating a position of the region of interest on the medical image, and the emphasis-degree setting unit preferably sets a transmittance of the figure to a relatively lower transmittance as the total time is relatively longer. Thus, the region of interest can be emphasized at an appropriate emphasis degree.

The emphasis processing unit preferably superposes a figure indicating a position of the region of interest on the medical image, and the emphasis-degree setting unit preferably sets a color of the figure to a relatively higher color intensity based on a color intensity index as the total time is relatively longer. Thus, the region of interest can be emphasized at an appropriate emphasis degree.

The emphasis processing unit preferably superposes a figure indicating a position of the region of interest on the medical image, and the emphasis-degree setting unit preferably sets a size of the figure to a relatively larger size as the total time is relatively longer. Thus, the region of interest can be emphasized at an appropriate emphasis degree.

The emphasis processing unit preferably superposes a frame-shaped figure that surrounds the region of interest on the medical image, and the emphasis-degree setting unit preferably sets a line thickness of the frame-shaped figure to be relatively thicker as the total time is relatively longer. Thus, the region of interest can be emphasized at an appropriate emphasis degree.

The emphasis-degree setting unit preferably relatively increases an increasing rate of the emphasis degree to the total time as the number of regions of interest that exist in the single medical image relatively increases. Thus, the region of interest can be emphasized at an appropriate emphasis degree.

The emphasis-degree setting unit preferably changes at least one of a minimum of the emphasis degree, a maximum of the emphasis degree, or an increasing rate of the emphasis degree to the total time, based on a position of the region of interest in the medical image. Thus, the region of interest can be emphasized at an appropriate emphasis degree.

The emphasis-degree setting unit preferably changes at least one of a minimum of the emphasis degree, a maximum of the emphasis degree, or an increasing rate of the emphasis degree to the total time, based on luminance of the region of interest or a difference between the luminance of the region of interest and luminance of a region outside the region of interest. Thus, the region of interest can be emphasized at an appropriate emphasis degree.

The emphasis-degree setting unit preferably changes at least one of a minimum of the emphasis degree, a maximum of the emphasis degree, or an increasing rate of the emphasis degree to the total time, based on color information of the region of interest or a difference between the color information of the region of interest and color information of a region outside the region of interest. Thus, the region of interest can be emphasized at an appropriate emphasis degree.

The emphasis-degree setting unit preferably changes at least one of a minimum of the emphasis degree, a maximum of the emphasis degree, or an increasing rate of the emphasis degree to the total time, based on a movement amount of the region of interest or a movement direction of the region of interest. Thus, the region of interest can be emphasized at an appropriate emphasis degree.

The medical image processing apparatus preferably further includes a display control unit that causes a display unit to sequentially display the time-series medical image in which the region of interest is emphasized. Thus, the display unit can report the region of interest.

The display control unit preferably causes the display unit which is at least one of a plurality of display units to sequentially display the time-series medical image in which the region of interest is emphasized. Thus, the at least one display unit among the plurality of display units can report the region of interest.

In order to achieve the above object, a diagnosis supporting apparatus according to an aspect is a diagnosis supporting apparatus including: the above-described medical image processing apparatus; and the display unit. According to this aspect, the display unit can display the time-series medical image in which the region of interest is emphasized at an appropriate emphasis degree.

In order to achieve the above object, an endoscope system according to an aspect is an endoscope system including: the above-described medical image processing apparatus; and an endoscope that captures the time-series medical image. According to this aspect, the region of interest in the medical image can be emphasized at an appropriate emphasis degree.

In order to achieve the above object, a medical image processing method according to an aspect is a medical image processing method including: an emphasis processing step for emphasizing a region of interest included in a time-series medical image at a set emphasis degree; a total-time measuring step for measuring a total time during which the region of interest is emphasized; and an emphasis-degree setting step for setting the emphasis degree to a relatively larger value as the total time is relatively longer.

According to this aspect, the region of interest in the medical image can be emphasized at an appropriate emphasis degree. A program causing a computer to execute the above medical image processing method is also included in this aspect.

According to the present invention, the region of interest in a medical image can be emphasized at an appropriate emphasis degree.

DESCRIPTION OF THE PREFERRED EMBODIMENTS

Hereinafter, preferred embodiments will be described in detail with reference to the accompanying drawings.

Overall Configuration of Endoscope System

Figure 1:
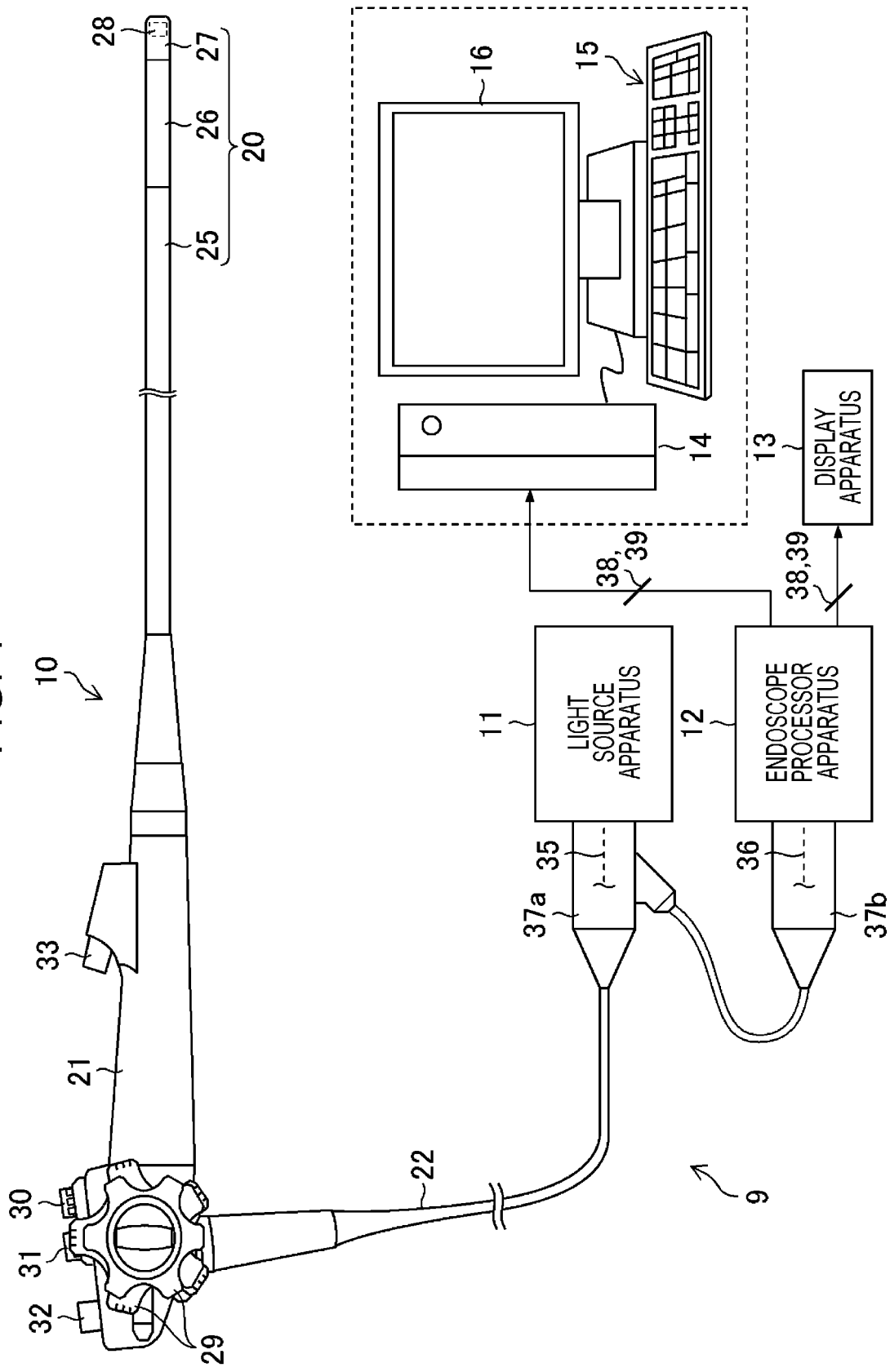
FIG. 1 illustrates an overview of an overall configuration of an endoscope system.

FIG. 1 illustrates an overview of an overall configuration of an endoscope system 9 including a medical image processing apparatus according to an embodiment. As illustrated in FIG. 1, the endoscope system 9 includes an endoscope 10, which is an electronic endoscope, a light source apparatus 11, an endoscope processor apparatus 12, a display apparatus 13, a medical image processing apparatus 14, an operating unit 15, and a display 16.

The endoscope 10 captures a time-series medical image and is a flexible endoscope, for example. The endoscope 10 has an insertion part 20, a handheld operating unit 21, and a universal cord 22. The insertion part 20 is inserted into a subject and has a distal end and a base end. The handheld operating unit 21 is disposed continuously with the base end side of the insertion part 20 and held by a user (physician) to perform various operations. The universal cord 22 is disposed continuously with the handheld operating unit 21.

The insertion part 20 is entirely formed to have a small diameter and an elongated shape. The insertion part 20 is constituted by a soft part 25, a bending part 26, and a distal end part 27, which are disposed continuously with each other in this order from the base end side to the distal end side. The soft part 25 has flexibility. The bending part 26 is bendable by an operation of the handheld operating unit 21. An imaging optical system (objective lens), which is not illustrated, an imaging element 28, and the like are incorporated in the distal end part 27.

The imaging element 28 is an imaging element of a complementary metal oxide semiconductor (CMOS) type or a charge coupled device (CCD) type. Image light of a part to be observed is incident on an imaging surface of the imaging element 28 through an observation window and the objective lens. The observation window, which is not illustrated, is open on a distal end surface of the distal end part 27, and the objective lens, which is not illustrated, is disposed behind the observation window. The imaging element 28 captures the image light of the part to be observed, which is incident on the imaging surface (converts the image light into an electric signal) and outputs an image signal.

The handheld operating unit 21 is provided with various operating members to be operated by a user. Specifically, the handheld operating unit 21 is provided with two types of bending operation knobs 29 to be used for a bending operation of the bending part 26, an air/water supply button 30 for air supply/water supply operations, and a suction button 31 for a suction operation. The handheld operating unit 21 is further provided with a still image pick-up command unit 32 for issuing a command for capturing a still image 39 of the part to be observed and a treatment tool introduction port 33 for inserting a treatment tool (not illustrated) into a treatment tool insertion path (not illustrated) that penetrates through the insertion part 20.

The universal cord 22 is a connection cord for connecting the endoscope 10 to the light source apparatus 11. The universal cord 22 contains a light guide 35 that penetrates through the insertion part 20, a signal cable 36, and a fluid tube (not illustrated). In addition, an end portion of the universal cord 22 is provided with a connector 37a that is connected to the light source apparatus 11 and a connector 37b that branches off from the connector 37a and is connected to the endoscope processor apparatus 12.

Since the connector 37a is connected to the light source apparatus 11, the light guide 35 and the fluid tube (not illustrated) are inserted into the light source apparatus 11. Thus, through the light guide 35 and the fluid tube (not illustrated), necessary illumination light, water, and gas are supplied from the light source apparatus 11 to the endoscope 10. As a result, the part to be observed is irradiated with the illumination light from an illumination window (not illustrated) on the distal end surface of the distal end part 27. In accordance with a pressing operation on the above-described air/water supply button 30, the gas or water is injected from an air/water supply nozzle (not illustrated) on the distal end surface of the distal end part 27 to the observation window (not illustrated) on the distal end surface.

Since the connector 37b is connected to the endoscope processor apparatus 12, the signal cable 36 is electrically connected to the endoscope processor apparatus 12. Thus, through the signal cable 36, an image signal of the part to be observed is output from the imaging element 28 of the endoscope 10 to the endoscope processor apparatus 12, and also, a control signal is output from the endoscope processor apparatus 12 to the endoscope 10.

The light source apparatus 11 supplies the illumination light through the connector 37a to the light guide 35 of the endoscope 10. As the illumination light, light in various wavelength ranges in accordance with an observation purpose, such as white light (light in a white wavelength range or light in a plurality of wavelength ranges), light in one or more specific wavelength ranges, or a combination thereof is selected. Note that the specific wavelength range is narrower than the white wavelength range.

A first example of the specific wavelength range is, for example, a blue range or a green range in a visible range. The wavelength range of the first example includes a wavelength range of greater than or equal to 390 nm and less than or equal to 450 nm or greater than or equal to 530 nm and less than or equal to 550 nm, and light of the first example has a peak wavelength in the wavelength range of greater than or equal to 390 nm and less than or equal to 450 nm or greater than or equal to 530 nm and less than or equal to 550 nm.

A second example of the specific wavelength range is, for example, a red range in a visible range. The wavelength range of the second example includes a wavelength range of greater than or equal to 585 nm and less than or equal to 615 nm or greater than or equal to 610 nm and less than or equal to 730 nm, and light of the second example has a peak wavelength in the wavelength range of greater than or equal to 585 nm and less than or equal to 615 nm or greater than or equal to 610 nm and less than or equal to 730 nm.

A third example of the specific wavelength range includes a wavelength range in which oxidized hemoglobin and reduced hemoglobin have different absorption coefficients, and light of the third example has a peak wavelength in the wavelength range in which oxidized hemoglobin and reduced hemoglobin have different absorption coefficients. The wavelength range of the third example includes a wavelength range of 400±10 nm, 440±10 nm, 470±10 nm, or greater than or equal to 600 nm and less than or equal to 750 nm, and light of the third example has a peak wavelength in the wavelength range of 400±10 nm, 440±10 nm, 470±10 nm, or greater than or equal to 600 nm and less than or equal to 750 nm.

A fourth example of the specific wavelength range is the wavelength range (from 390 nm to 470 nm) of excitation light that is used for observing fluorescence (fluorescence observation) emitted by a fluorescent material in a living body and that excites the fluorescent material.

A fifth example of the specific wavelength range is the wavelength range of infrared light. The wavelength range of the fifth example includes a wavelength range of greater than or equal to 790 nm and less than or equal to 820 nm or greater than or equal to 905 nm and less than or equal to 970 nm, and light of the fifth example has a peak wavelength in the wavelength range of greater than or equal to 790 nm and less than or equal to 820 nm or greater than or equal to 905 nm and less than or equal to 970 nm.

The endoscope processor apparatus 12 controls operations of the endoscope 10 through the connector 37b and the signal cable 36. In addition, based on the image signal acquired from the imaging element 28 of the endoscope 10 through the connector 37b and the signal cable 36, the endoscope processor apparatus 12 generates a moving image 38 that is a time-series medical image formed of time-series frame images 38a (see FIG. 2) including a photographic subject image. The frame rate of the moving image 38 is, for example, 30 fps (frame per second).

Furthermore, if the still image pick-up command unit 32 is operated in the handheld operating unit 21 of the endoscope 10, concurrently with the generation of the moving image 38, the endoscope processor apparatus 12 acquires one frame image 38a in the moving image 38 as the still image 39 in accordance with the timing of an imaging command.

The moving image 38 and the still image 39 are medical images obtained by imaging the inside of the subject, that is, a living body. In addition, if the moving image 38 and the still image 39 are images obtained with the above-described light in the specific wavelength range (special light), both are special light images. In addition, the endoscope processor apparatus 12 outputs the generated moving image 38 and the still image 39 to each of the display apparatus 13 and the medical image processing apparatus 14.

Note that the endoscope processor apparatus 12 may generate (acquire) the special light image having information on the above-described specific wavelength range, based on a usual light image obtained with the above-described white light. In this case, the endoscope processor apparatus 12 functions as a special light image acquiring unit. Then, the endoscope processor apparatus 12 obtains a signal in the specific wavelength range by performing calculation based on RGB color information of red, green, and blue or CMY color information of cyan, magenta, and yellow included in the usual light image.

Based on, for example, at least one of the usual light image obtained with the above-described white light or the special light image obtained with the above-described light in the specific wavelength range (special light), the endoscope processor apparatus 12 may generate a feature quantity image such as a known oxygen saturation image. In this case, the endoscope processor apparatus 12 functions as a feature quantity image generating unit. Note that each of the moving image 38 and the still image 39 including the above-described in-living-body image, the usual light image, the special light image, and the feature quantity image is a medical image obtained by converting results of imaging or measuring of a human body into an image for the purpose of image diagnosis or inspection.

The display apparatus 13 is connected to the endoscope processor apparatus 12 and displays the moving image 38 and the still image 39 input from the endoscope processor apparatus 12. A user operates the insertion part 20 back and forth, for example, while viewing the moving image 38 displayed on the display apparatus 13, and, if a lesion or the like is found at the part to be observed, the user operates the still image pick-up command unit 32 to capture a still image of the part to be observed for diagnosis, biopsy, or the like.

Configuration of Medical Image Processing Apparatus

The medical image processing apparatus 14 reports a region of interest included in a time-series medical image to a user, and, for example, a personal computer is used as the medical image processing apparatus 14 in this embodiment. In addition, a keyboard, a mouse, or the like connected to the personal computer via wired or wireless connection is used as the operating unit 15, and any monitor, such as a liquid crystal monitor that can be connected to the personal computer, is used as the display 16 (example of a display unit).

Figure 2:
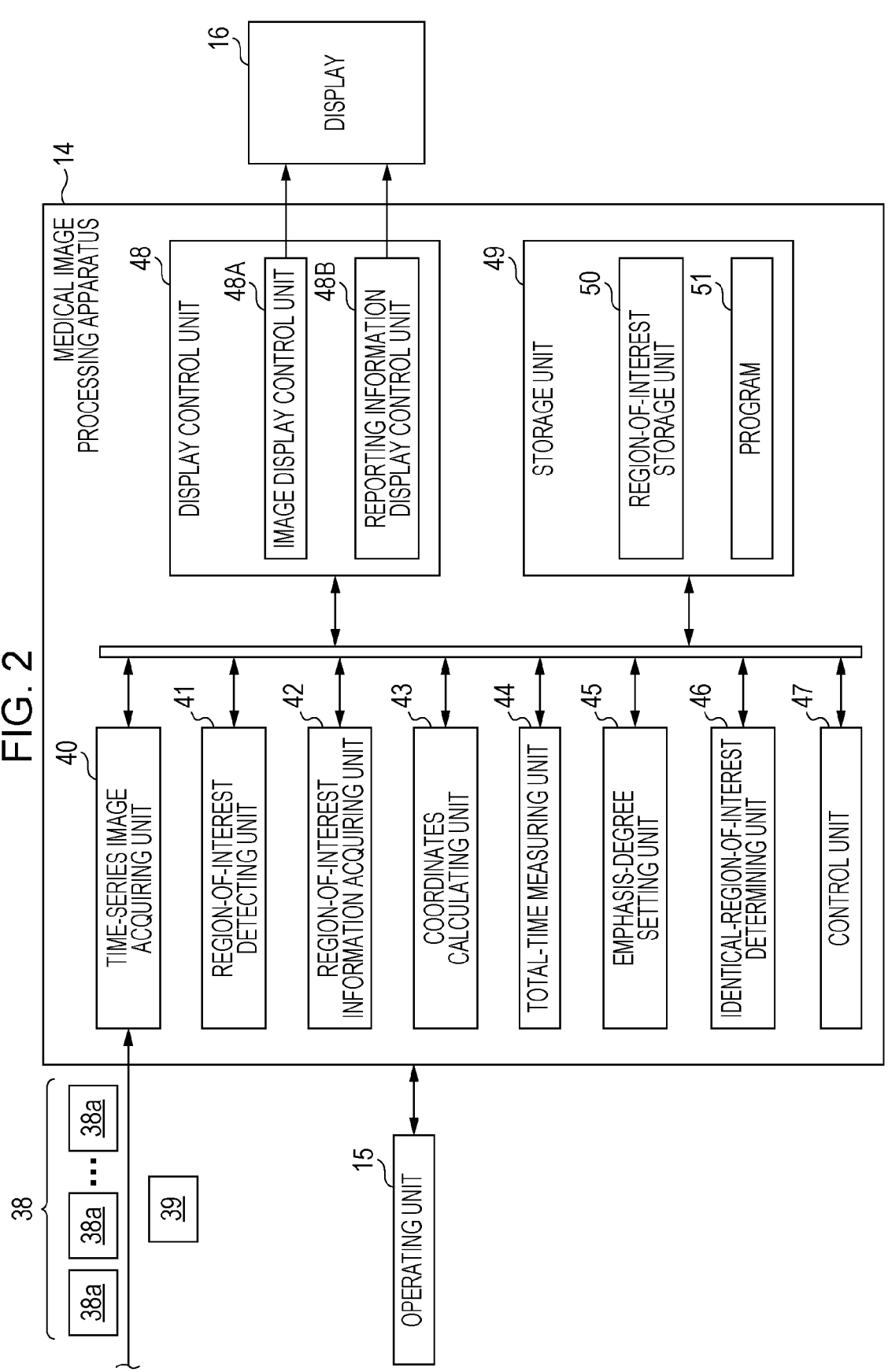
FIG. 2 is a block diagram illustrating an electric configuration of a medical image processing apparatus.

FIG. 2 is a block diagram illustrating an electric configuration of the medical image processing apparatus 14. The medical image processing apparatus 14 illustrated in FIG. 2 is mainly constituted by a time-series image acquiring unit 40, a region-of-interest detecting unit 41, a region-of-interest information acquiring unit 42, a coordinates calculating unit 43, a total-time measuring unit 44, an emphasis-degree setting unit 45, an identical-region-of-interest determining unit 46, a control unit 47, a display control unit 48, and a storage unit 49.

Based on a program (medical image processing program) 51 stored in the storage unit 49, the control unit 47 generally controls the time-series image acquiring unit 40, the region-of-interest detecting unit 41, the region-of-interest information acquiring unit 42, the coordinates calculating unit 43, the total-time measuring unit 44, the emphasis-degree setting unit 45, the identical-region-of-interest determining unit 46, and the display control unit 48 and functions as part of these units.

The storage unit 49 is a part that stores detection results obtained by the region-of-interest detecting unit 41 and stores a captured still image 39, and also stores information or the like related to various controls of a region-of-interest storage unit 50 that stores a feature quantity and a total time of the region of interest in association with each other, the program 51, and the medical image processing apparatus 14.

The time-series image acquiring unit 40 acquires, from the endoscope processor apparatus 12 (FIG. 1), the moving image 38 (moving image 38 captured by the endoscope 10 in this example), formed of the time-series frame images 38a including a photographic subject image, by using an image input/output interface, which is not illustrated, connected to the endoscope processor apparatus 12 via wired or wireless connection. In addition, if the above-described still image 39 is captured while the moving image 38 is being captured by the endoscope 10, the time-series image acquiring unit 40 acquires the moving image 38 and the still image 39 from the endoscope processor apparatus 12.

Note that, instead of directly acquiring the moving image 38 from the endoscope processor apparatus 12, the time-series image acquiring unit 40 may acquire the moving image 38 via any information storage medium, such as a memory card or a hard disk apparatus. In addition, the time-series image acquiring unit 40 may acquire, via the Internet, the moving image 38 uploaded on a server, database, or the like on the Internet.

The region-of-interest detecting unit 41 is an image processing unit that detects the region of interest from the moving image 38 captured during observation of the inside of the subject. The region-of-interest detecting unit 41 calculates a feature quantity of the frame images 38a (or the frame images 38a decimated at certain intervals) of the moving image 38 and includes a convolutional neural network (CNN) that performs recognition processing of the region of interest within an image.

As examples of the region of interest, there are a polyp, cancer, a colon diverticulum, inflammation, an endoscopic mucosal resection (EMR) scar, an endoscopic submucosal dissection (ESD) scar, a clipped part, a bleeding point, perforation, an atypical vessel, a treatment tool, and the like.

The region-of-interest detecting unit 41 can further acquire a recognition result of, for example, category classification as to whether the detected region of interest belongs to which of a plurality of categories about the lesion, such as "tumorous", "non-tumorous", and "others".

Note that the region-of-interest detecting unit 41 is not limited to the one that detects the region of interest by the CNN, but may detect the region of interest by analyzing a feature quantity such as the color, pixel value gradient, shape, or size in the image through image processing.

The region-of-interest information acquiring unit 42 (an example of a feature quantity calculating unit) acquires region-of-interest information of the region of interest detected by the region-of-interest detecting unit 41. The region-of-interest information can be, for example, information of coordinates of a contour of the region of interest in the image and a feature quantity of the region of interest. The coordinates information may be included in the feature quantity.

The coordinates calculating unit 43 calculates coordinates information indicating the position of the region of interest in the image detected by the region-of-interest detecting unit 41. The coordinates calculating unit 43 calculates, for example, one or more pieces of coordinates information on the contour of a polygon or a circle that surrounds a region of interest. As the coordinates information, coordinates of vertexes of the polygon or coordinates of midpoints of sides of the polygon may be calculated, or coordinates of points at which a circumference of the circle is equally divided into a plurality of parts may be calculated.

The total-time measuring unit 44 measures, as a total time, a total detection time during which the region of interest is detected by the region-of-interest detecting unit 41. The emphasis-degree setting unit 45 sets an emphasis degree to a relatively larger value as the total time is relatively longer. For the emphasis degree, a minimum, a maximum, and an increasing rate of the emphasis degree with respect to the total time are determined in advance. Thus, from the total time, the emphasis degree can be calculated. The emphasis-degree setting unit 45 calculates and sets the emphasis degree in accordance with the region of interest from the total time measured by the total-time measuring unit 44.

If a plurality of regions of interest are detected by the region-of-interest detecting unit 41, the total-time measuring unit 44 measures the total time of each of the regions of interest, and the emphasis-degree setting unit 45 sets the emphasis degree of the region of interest in accordance with the total time of the region of interest.

Note that the region of interest is emphasized at the emphasis degree set by the emphasis-degree setting unit 45, as described later. The total-time measuring unit 44 may measure the total time during which the region of interest is emphasized.

The identical-region-of-interest determining unit 46 determines whether the region of interest included in a medical image in the moving image 38 is identical with a region of interest that is emphasized in a previous medical image, which precedes the above medical image in time series. The identical-region-of-interest determining unit 46 may also determine whether the region of interest included in a medical image in the moving image 38 is identical with a region of interest that is detected by the region-of-interest detecting unit 41 in a previous medical image, which precedes the above medical image in time series. This determination is performed by using the feature quantity of the region of interest acquired by the region-of-interest information acquiring unit 42.

The display control unit 48 includes an image display control unit 48A and a reporting information display control unit 48B. The image display control unit 48A outputs the moving image 38 acquired by the time-series image acquiring unit 40 to the display 16 and causes the display 16 to display the moving image 38. That is, the display 16 sequentially displays a plurality of frame images 38a.

Based on the coordinates information calculated by the coordinates calculating unit 43, and based on the emphasis degree set by the emphasis-degree setting unit 45, the reporting information display control unit 48B outputs reporting information for reporting the region of interest to the display 16. Herein, as the reporting information, a figure indicating the position of the region of interest is superposed at the position of the region of interest. Thus, at the position of the region of interest in the moving image 38 displayed on the display 16, the figure in accordance with the total time of the region of interest is superposed. Thus, the region of interest is emphasized at the set emphasis degree by the superposed figure.

In this manner, the medical image processing apparatus 14 and the display 16 function as a diagnosis supporting apparatus.

Medical Image Processing Method: First Embodiment

A medical image processing method using the endoscope system 9 will be described. The medical image processing method is performed by the control unit 47 executing the program 51 stored in the storage unit 49.

Figure 3:
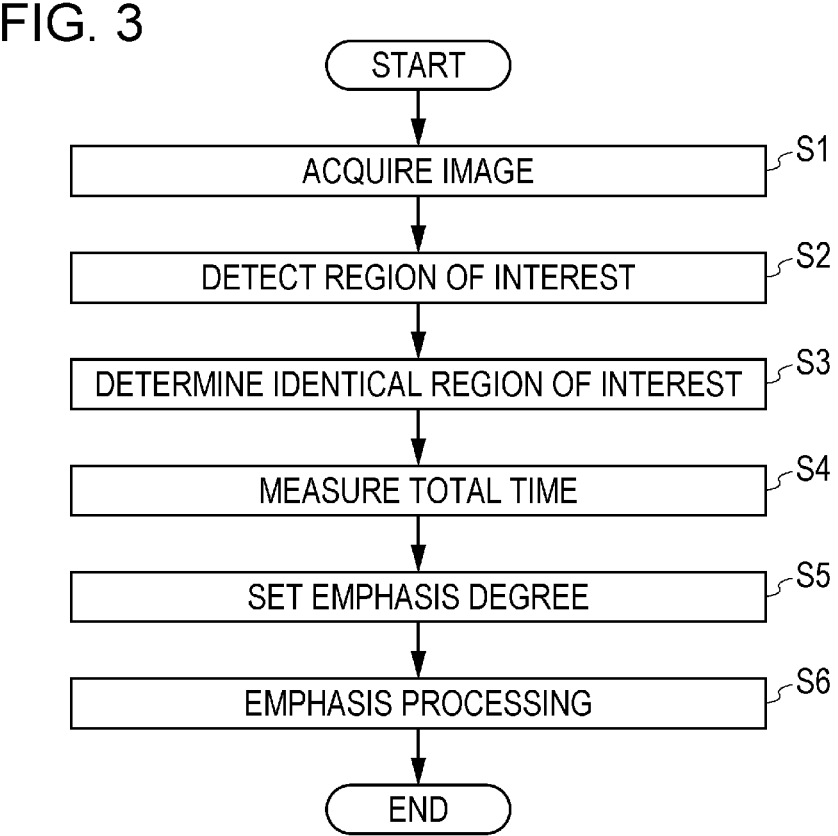
FIG. 3 is a flowchart illustrating an example of each process of a medical image processing method according to a first embodiment.

FIG. 3 is a flowchart illustrating an example of each process of the medical image processing method according to a first embodiment. The medical image processing method includes an image acquisition step (step S1), a region-of-interest detection step (step S2), an identical region-of-interest determining step (step S3), a total-time measuring step (step S4), an emphasis-degree setting step (step S5), and an emphasis processing step (step S6).

In step S1, the time-series image acquiring unit 40 acquires a frame image 38a in a moving image 38 captured by the endoscope 10. This frame image 38a is set as a first medical image.

In step S2, the region-of-interest detecting unit 41 detects a region of interest from the first medical image acquired in step S1. The region of interest detected from the first medical image is set as a first region of interest.

In step S3, the region-of-interest information acquiring unit 42 acquires a feature quantity of the first region of interest from the first medical image. In addition, the region-of-interest information acquiring unit 42 reads, from the region-of-interest storage unit 50, a feature quantity of a second region of interest emphasized (detected) in a second medical image, which is a frame image 38a one frame before the first medical image in the moving image 38.

Furthermore, the identical-region-of-interest determining unit 46 determines whether the first region of interest is identical with the second region of interest from a similarity degree between the feature quantity of the first region of interest and the feature quantity of the second region of interest.

In step S4, the total-time measuring unit 44 measures a total time of the first region of interest. The total time is a time that is started to be measured from the timing the region of interest is emphasized. The total time may also be a time that is started to be measured from the timing the region of interest is detected. The total time may be counted as the number of frames of a time-series image from the timing the region of interest is emphasized or the timing the region of interest is detected.

If it is determined in step S3 that the first region of interest is not identical with the second region of interest, the total-time measuring unit 44 determines that the first region of interest is a newly detected region of interest and newly starts to measure the total time.

On the other hand, if it is determined in step S3 that the first region of interest is identical with the second region of interest, the total-time measuring unit 44 measures the total time of the first region of interest by taking over the total time of the second region of interest. That is, the total-time measuring unit 44 reads the total time of the second region of interest from the region-of-interest storage unit 50 and adds, to the read total time, the time that equals to one frame from the second medical image to the first medical image.

In step S5, the emphasis-degree setting unit 45 sets an emphasis degree of the first region of interest.

If it is determined in step S3 that the first region of interest is not identical with the second region of interest, since measurement of the total time has only newly started, the emphasis-degree setting unit 45 sets the emphasis degree of the first region of interest to a predetermined minimum.

On the other hand, if it is determined in step S3 that the first region of interest is identical with the second region of interest, the emphasis-degree setting unit 45 sets the emphasis degree of the first region of interest in accordance with the total time that is measured by taking over the total time of the second region of interest.

Note that the emphasis-degree setting unit 45 may read an emphasis degree of the second region of interest from the region-of-interest storage unit 50 and may calculate the emphasis degree of the first region of interest from the read emphasis degree of the second region of interest, an elapsed time from the second medical image to the first medical image, and a predetermined increasing rate of the emphasis degree.

Lastly, in step S6, the display control unit 48 (an example of an emphasis processing unit) emphasizes the first region of interest included in the first medical image at the set emphasis degree. Herein, the image display control unit 48A outputs the first medical image to the display 16 and causes the display 16 to display the first medical image. In addition, based on coordinates information calculated by the coordinates calculating unit 43, and based on the emphasis degree set by the emphasis-degree setting unit 45, the reporting information display control unit 48B outputs reporting information for reporting the first region of interest to the display 16. Thus, a figure in accordance with the total time of the first region of interest is superposed at the position of the first region of interest in the first medical image. Accordingly, the first region of interest is emphasized at the set emphasis degree by using the superposed figure.

In addition, in step S6, the control unit 47 stores the feature quantity, the total time, and the emphasis degree of the first region of interest in the region-of-interest storage unit 50 in association with the first region of interest.

In the above manner, according to the medical image processing method, the region of interest in the medical image can be appropriately reported.

Emphasis Processing

Figure 4:
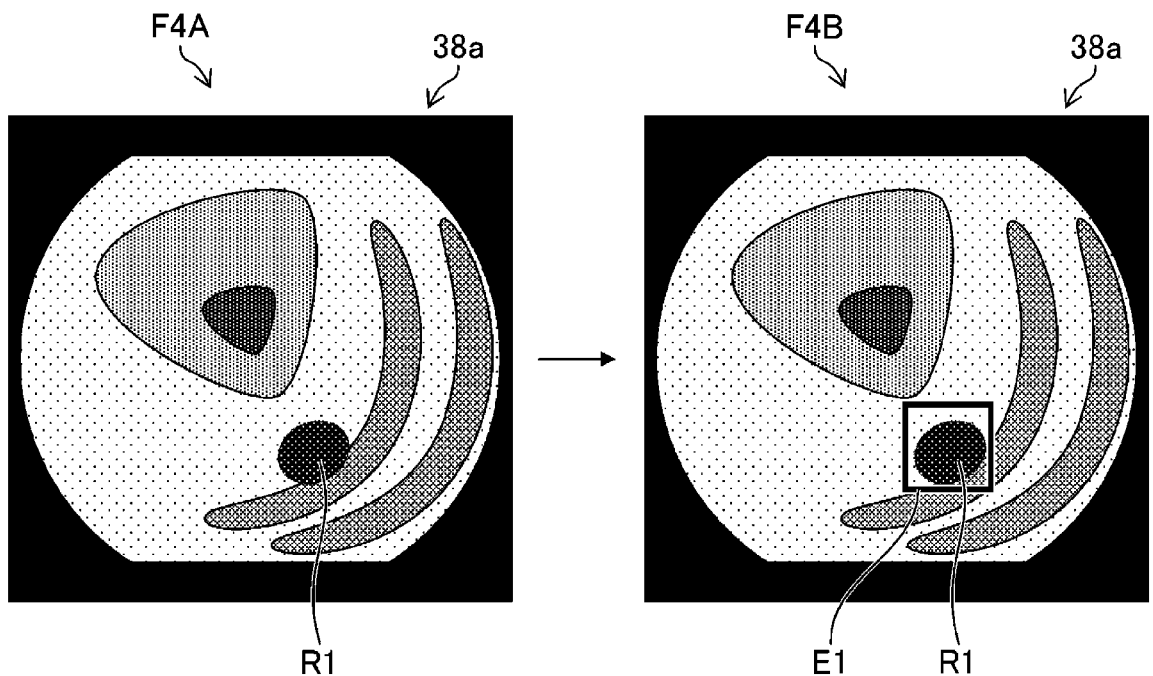
FIG. 4 illustrates an example of emphasis processing.

FIG. 4 illustrates an example of emphasis processing performed by the display control unit 48. F4A illustrated in FIG. 4 illustrates a frame image 38a in which a region of interest R1 is detected. In addition, F4B illustrated in FIG. 4 illustrates a frame image 38a in which a frame-shaped figure E1 that surrounds the region of interest R1 is superposed on the frame image 38a illustrated in F4A at the position of the region of interest R1. In this manner, by superposing the figure at the position of the region of interest R1, the display control unit 48 can emphasize the region of interest R1.

The shape of the frame-shaped figure to be superposed on the image is not limited to a rectangle but may also be a circle, an ellipse, or a polygon. In addition, the figure to be superposed on the image may also be an arrow indicating the region of interest or the like.

Figure 5:
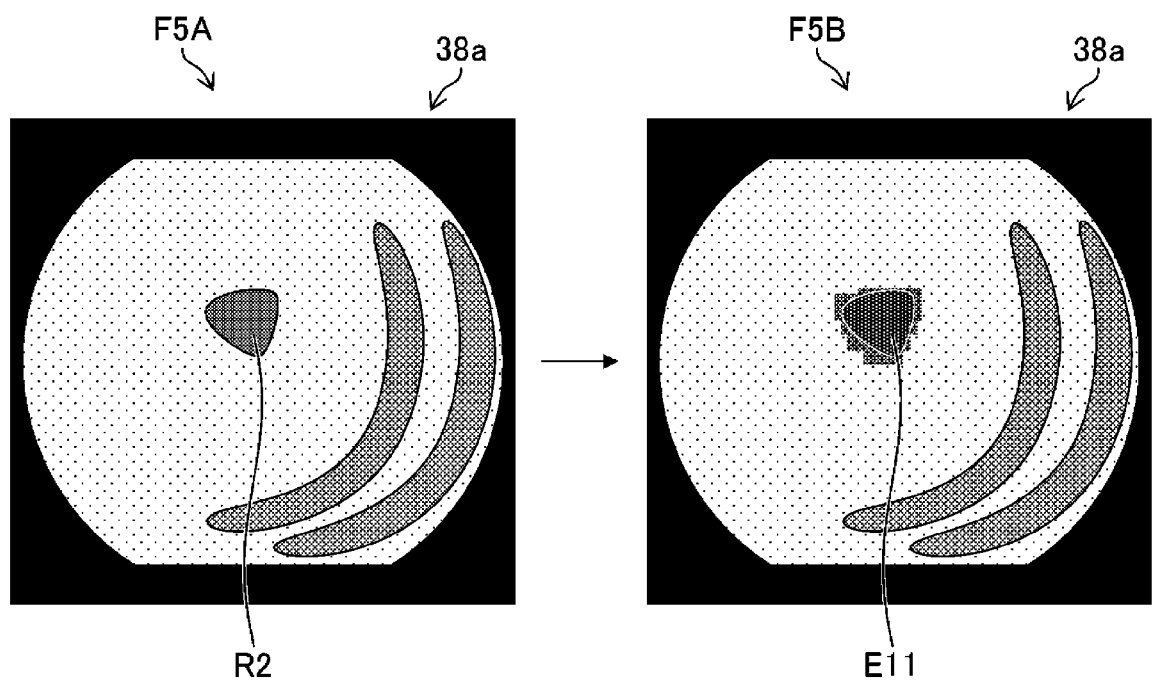
FIG. 5 illustrates another example of emphasis processing.

In addition, FIG. 5 illustrates another example of emphasis processing. F5A illustrated in FIG. 5 illustrates a frame image 38a in which a region of interest R2 is detected. In addition, F5B illustrated in FIG. 5 illustrates a frame image 38a in which a figure E11 is superposed on the frame image 38a illustrated in F5A at the position of the region of interest R2. The figure E11 has substantially the same shape as the region of interest R2, and brightness thereof as a pixel value is different from that of the region of interest R2. In the above manner, the display control unit 48 may superpose the figure for which the pixel value is changed at the position of the region of interest.

Processing for making the pixel value of the figure to be superposed at the position of the region of interest differ from the pixel value of the region of interest is not limited to processing for changing the brightness but may also be hue changing processing, saturation changing processing, contrast processing, negative/positive reversing processing, filtering processing, frequency processing, and the like. These kinds of processing are preferably processing by which the region of interest becomes more outstanding than a region outside the region of interest.

Increasing Rate of Emphasis Degree

Figure 6:
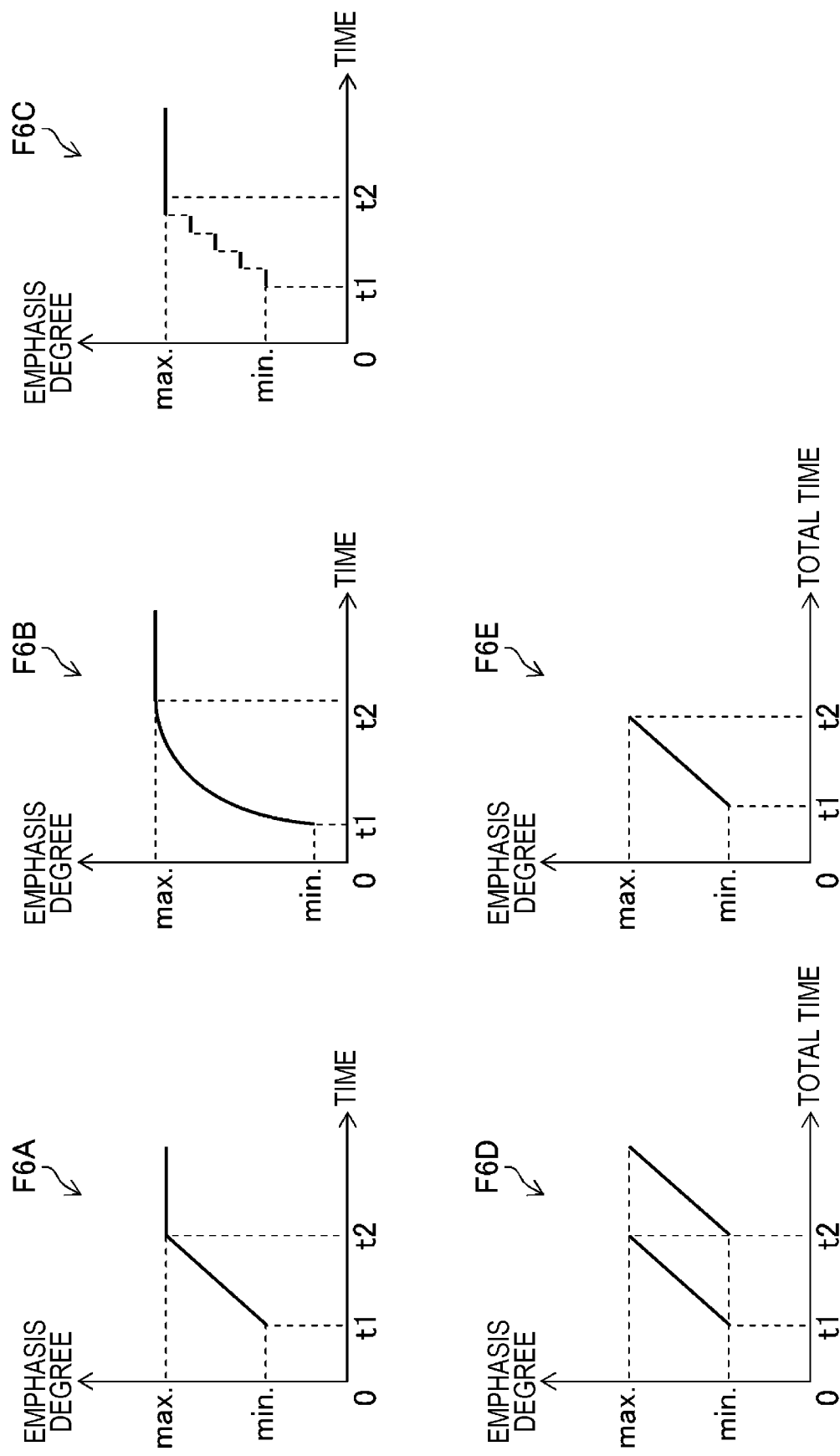
FIG. 6 is a graph illustrating an example of a relationship between a total time of a region of interest and an emphasis degree.

FIG. 6 is a graph illustrating an example of a relationship between a total time of a region of interest and an emphasis degree to be set, in which the horizontal axis represents time, and the vertical axis represents emphasis degree. FIG. 6 illustrates five examples in F6A to F6E.

In F6A to F6E, a time t1 is a timing at which the region of interest is detected. As illustrated in F6A to F6E, the emphasis degree is set to a minimum at the time t1 and is set to a maximum at a time t2, which is a timing after the time t1. In addition, the emphasis degree is set to a relatively larger value as the total time from the time t1 until the time t2 is relatively longer. Note that the frame image 38a is displayed as it is if the emphasis degree is 0.

The emphasis degree may be increased in proportion to the total time as illustrated in F6A or may be increased exponentially with respect to the total time as illustrated in F6B. Alternatively, the total time may be increased in a stepwise manner as illustrated in F6C. That is, the increasing rate of the emphasis degree to the total time (hereinafter referred to as increasing rate) is not limited to a fixed value but may be a value obtained by a function with respect to the total time.

The minimum, the maximum, and the increasing rate of the emphasis degree are stored in the storage unit 49 as predetermined fixed values. In addition, the minimum, the maximum, and the increasing rate of the emphasis degree may be changed as appropriate by using the feature quantity obtained from an image. Alternatively, a user may set desired values.

After the emphasis degree reaches the maximum, as illustrated in F6A to F6C, the maximum may be maintained as it is. Until a fixed time elapses, by placing emphasis by setting the emphasis degree at the maximum, a user is likely to recognize the region of interest.

Alternatively, as illustrated in F6D, after the emphasis degree reaches the maximum, the emphasis degree may be repeatedly increased again from the minimum. In this case, a blinking portion where the emphasis degree is repeatedly increased is likely to attract attention, and thus, a user is prevented from missing the region of interest.

Further alternatively, as illustrated in F6E, after the emphasis degree reaches the maximum, the emphasis processing may end, that is, the emphasis degree may be set to 0. In this case, the emphasis processing can be prevented from being performed too long, which may interrupt observation of the region of interest by a user.

These manners after the emphasis degree reaches the maximum may be selected as appropriate in accordance with the region of interest. Alternatively, a user may set a desired manner.

Change of Reporting Information

Figure 7:
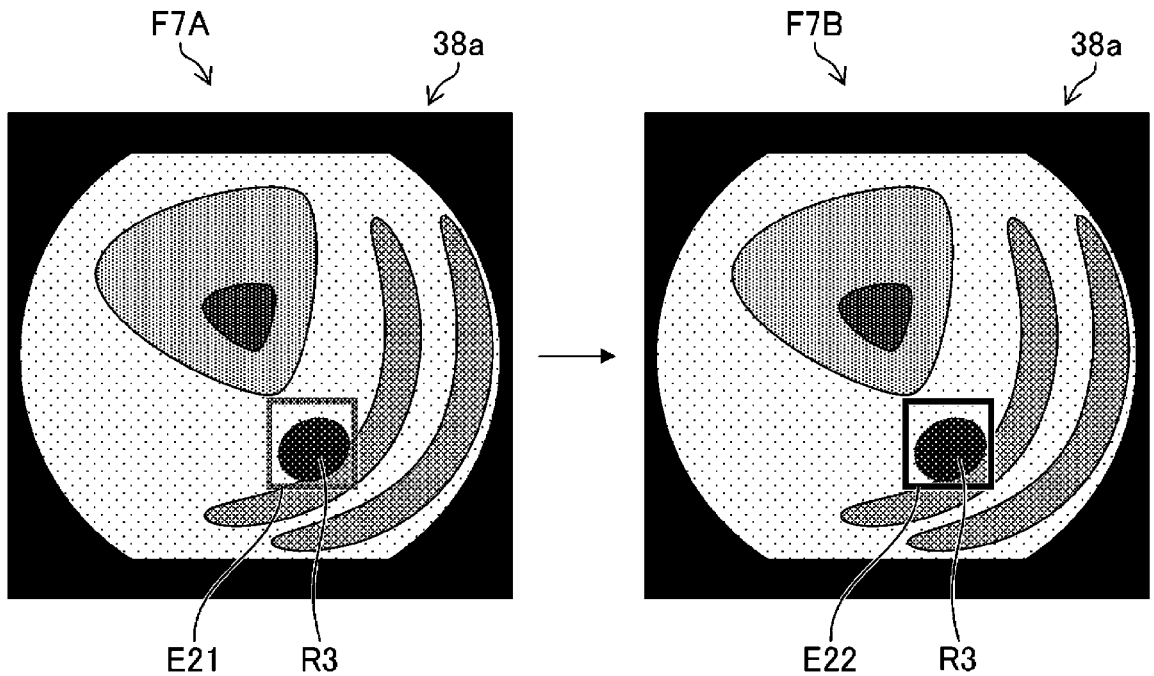
FIG. 7 illustrates an example of change of a figure in accordance with an emphasis degree.

FIG. 7 illustrates an example of change of a figure in accordance with an emphasis degree. F7A illustrated in FIG. 7 illustrates a frame image 38a on which a figure E21 is superposed. The figure E21 is a frame-shaped figure that surrounds a region of interest R3 and has a minimum emphasis degree. In addition, F7B illustrated in FIG. 7 illustrates a frame image 38a on which a figure E22 is superposed. The figure E22 is a frame-shaped figure that surrounds the region of interest R3 and has a maximum emphasis degree. The frame image 38a illustrated in F7B is a frame image subsequent to the frame image 38a illustrated in F7A in time series.

The figure E21 and the figure E22 are figures having the same line thickness and color and have different transmittances. Herein, by setting the transmittance of the figure to a relatively lower transmittance as the total time is relatively longer, the emphasis-degree setting unit 45 sets the emphasis degree to a relatively larger value as the total time is relatively longer. Thus, the transmittance of the figure E22 is relatively lower than the transmittance of the figure E21.

Figure 8:
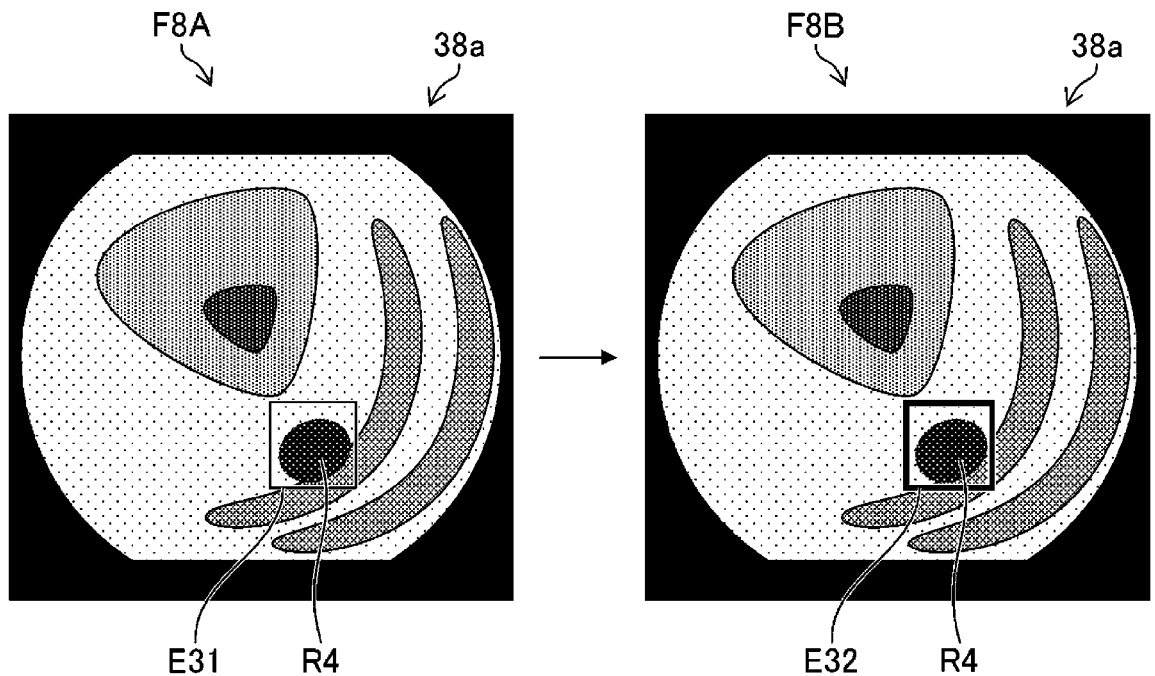
FIG. 8 illustrates another example of change of a figure in accordance with an emphasis degree.

FIG. 8 illustrates another example of change of a figure in accordance with an emphasis degree. F8A illustrated in FIG. 8 illustrates a frame image 38a on which a figure E31 is superposed. The figure E31 is a frame-shaped figure that surrounds a region of interest R4 and has a minimum emphasis degree. In addition, F8B illustrated in FIG. 8 illustrates a frame image 38a on which a figure E32 is superposed. The figure E32 is a frame-shaped figure that surrounds the region of interest R4 and has a maximum emphasis degree. The frame image 38a illustrated in F8B is a frame image subsequent to the frame image 38a illustrated in F8A in time series.

The figure E31 and the figure E32 are figures having the same transmittance and color and have different line thicknesses. Herein, by setting the line thickness of the figure to be relatively thicker as the total time is relatively longer, the emphasis-degree setting unit 45 sets the emphasis degree to a relatively larger value as the total time is relatively longer. Thus, the line of the figure E32 is relatively thicker than the line of the figure E31.

Figure 9:
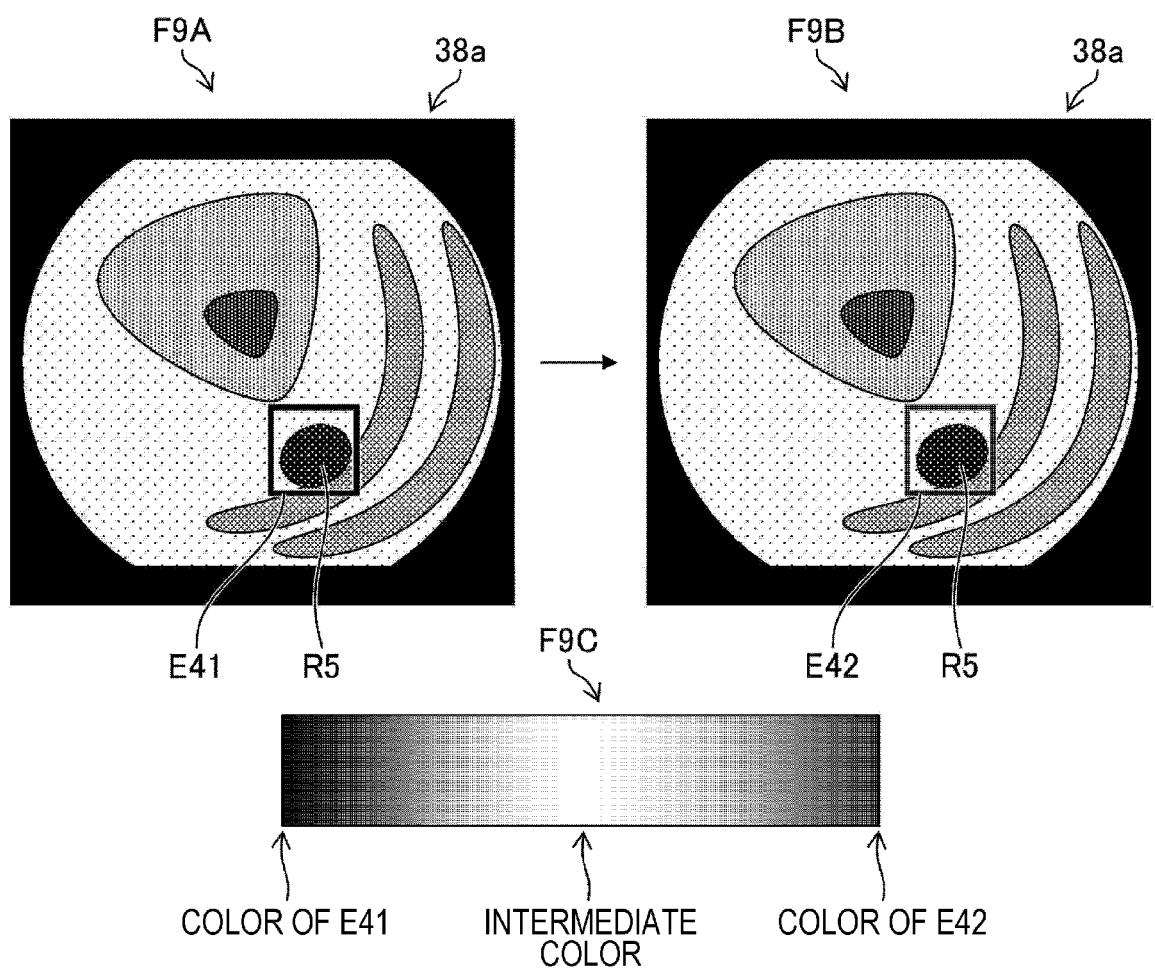
FIG. 9 illustrates another example of change of a figure in accordance with an emphasis degree.

FIG. 9 illustrates another example of change of a figure in accordance with an emphasis degree. F9A illustrated in FIG. 9 illustrates a frame image 38a on which a figure E41 is superposed. The figure E41 is a frame-shaped figure that surrounds a region of interest R5 and has a minimum emphasis degree. In addition, F9B illustrated in FIG. 9 illustrates a frame image 38a on which a figure E42 is superposed. The figure E42 is a frame-shaped figure that surrounds the region of interest R5 and has a maximum emphasis degree. The frame image 38a illustrated in F9B is a frame image subsequent to the frame image 38a illustrated in F9A in time series.

The figure E41 and the figure E42 are figures having the same transmittance and line thickness and have different colors (color temperatures). Herein, by setting the color of the figure to a color of a higher color intensity based on a given color intensity index as the total time is relatively longer, the emphasis-degree setting unit 45 sets the emphasis degree to a relatively larger value as the total time is relatively longer. Thus, the color of the figure E42 has a relatively higher color intensity based on a given color intensity index than the color of the figure E41.

F9C illustrated in FIG. 9 illustrates transition from the color of the figure E41 to the color of the figure E42. The intermediate color between the color of the figure E41 and the color of the figure E42 may be calculated by changing the equal ratio, equal difference, or ratio of the colors.

The emphasis-degree setting unit 45 may set the emphasis degree to a relatively larger value as the total time is relatively longer by acquiring the color of the frame image 38a and setting the color of the figure to a color having a relatively higher contrast to the color of the frame image 38a as the total time is relatively longer. The color of the frame image 38a differs depending on the color of the inside of the subject and the wavelength of illumination light supplied from the light source apparatus 11. Thus, in accordance with the acquired color of the frame image 38a, the color of the figure E41 and the color of the figure E42 are determined as appropriate.

Alternatively, instead of the color of the figure, at least one of the brightness or the saturation of the figure may be changed. The change preferably makes the region of interest seem more outstanding as the total time is longer. In this manner, by changing at least one of the color, the brightness, or the saturation of the figure, emphasis processing can be performed by taking into account the color difference from the periphery, the light source, and the like.

In addition, at least one of the size or the shape of the figure may be changed. Also in this case, the change preferably makes the region of interest seem more outstanding as the total time is longer.

Total Time

The total time measured by the total-time measuring unit 44 indicates, for example, the time during which a region of interest is continuously detected from the initial detection timing.

Figure 10:
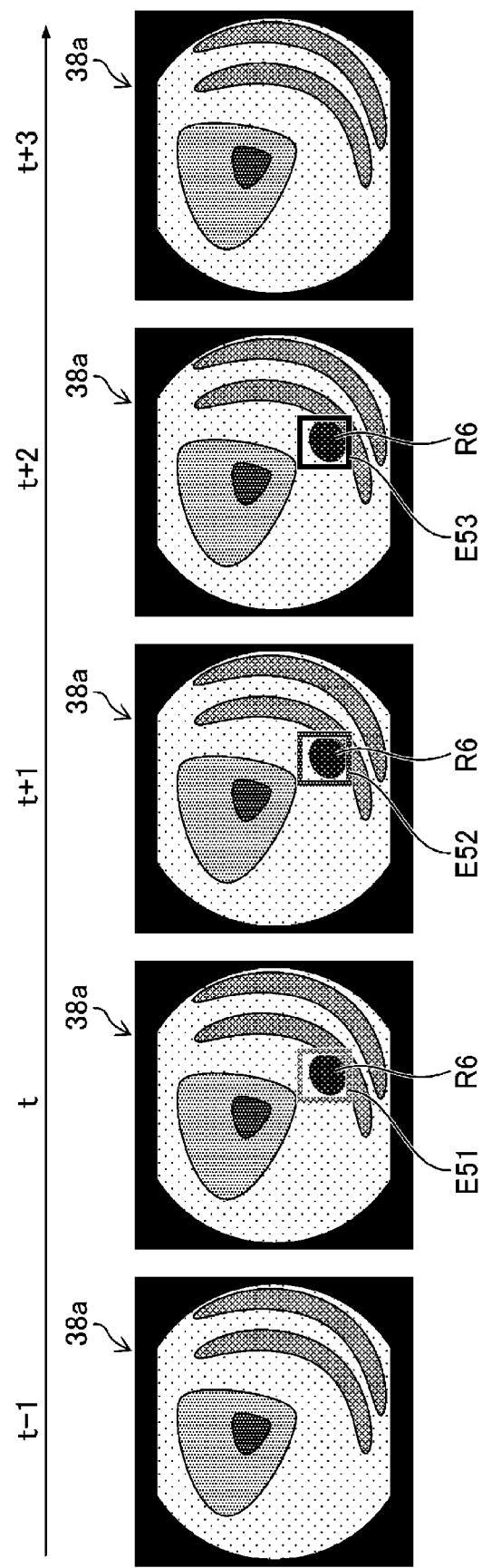
FIG. 10 is a drawing for explaining the total time.

FIG. 10 is a drawing for explaining the total time. FIG. 10 illustrates examples of frame images 38a at time t−1, time t, time t+1, time t+2, and time t+3. Herein, no region of interest is detected in the frame image 38a at time t−1. In addition, an identical region of interest R6 is detected in the frame images 38a at time t, time t+1, and time t+2. In accordance with this, a figure E51, a figure E52, and a figure E53 having a frame shape that surrounds the region of interest R6 are superposed on the frame images 38a at time t, time t+1, and time t+2, respectively.

In the examples illustrated in FIG. 10, the total time of the region of interest R6 in the frame image 38a at time t is 0. The total time of the region of interest R6 in the frame image 38a at time t+1 is (t+1)−t=1, and the total time of the region of interest R6 in the frame image 38a at time t+2 is (t+2)−t=2.

Thus, the emphasis degree (minimum) in accordance with the total time 0 is set for the figure E51, the emphasis degree in accordance with the total time 1 is set for the figure E52, and the emphasis degree in accordance with the total time 2 is set for the figure E53.

In addition, as illustrated in FIG. 10, no region of interest is detected in the frame image 38a at time t+3. Thus, at time t+3, the total time of the region of interest R6 is reset to 0, and emphasis processing is reset.

Note that the total time and the emphasis processing are not limited to being reset immediately upon stopping of detection of the region of interest.

In the moving image 38 captured by the endoscope 10, in some cases, the region of interest is hidden from folds of intestines or the like and is not captured in the image at a certain timing. If the region of interest that has been hidden is found again, the newly found region of interest may be determined as another region of interest, and the emphasis degree may be reset, in which case a user may not pay attention to the region of interest.

In addition, the endoscope 10 is difficult to operate, and it is difficult to make the region of interest remain constantly in the observation image. Thus, if support is provided by recognizing the region of interest as a different region of interest every time the region of interest becomes out of the screen, a user's thought may be interrupted.

Furthermore, if the observation window (not illustrated) on the distal end surface of the distal end part 27 is soiled, for example, the region-of-interest detecting unit 41 cannot detect the region of interest in some cases.

Thus, even if the detection is stopped, information on the region of interest is held for a certain time Tk, and, upon detection of the identical region of interest later, the emphasis degree may be taken over.

Figure 11:
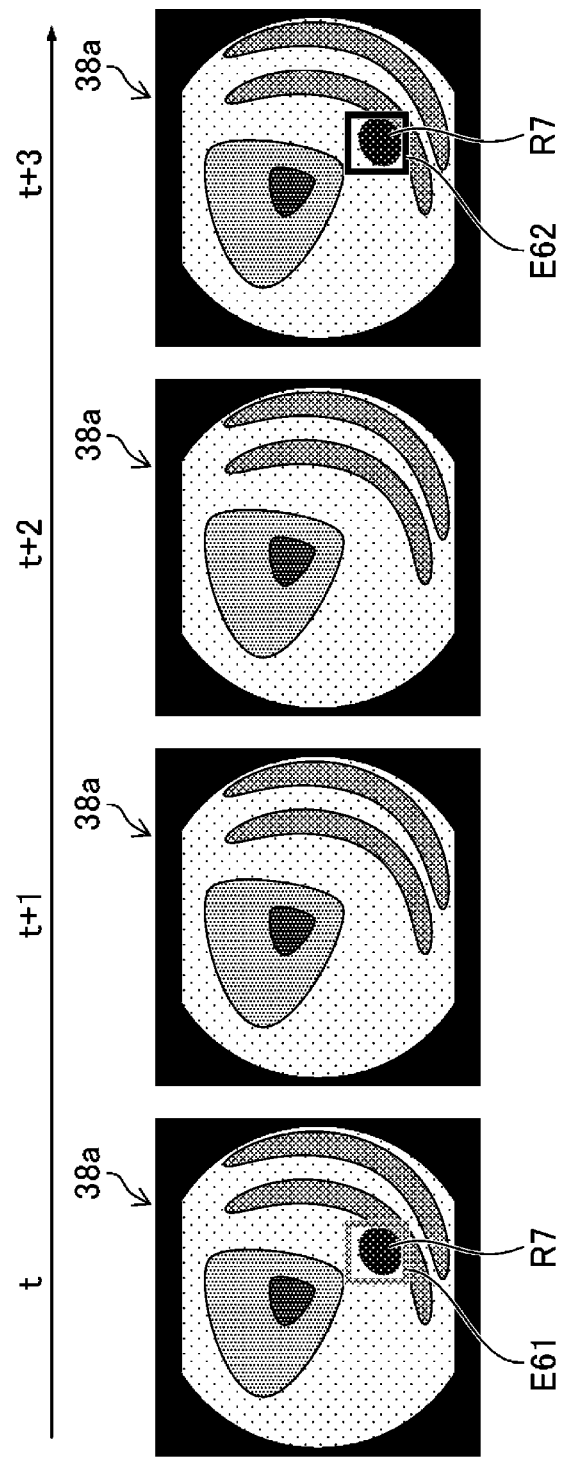
FIG. 11 is a drawing for explaining the total time.

FIG. 11 is a drawing for explaining the total time. FIG. 11 illustrates examples of frame images 38a at time t, time t+1, time t+2, and time t+3. As illustrated in FIG. 11, a region of interest R7 is detected in the frame image 38a at time t. In accordance with this, a figure E61 having a frame shape that surrounds the region of interest R7 is superposed on the frame image 38a at time t. At time t, the total time of the region of interest R7 is Tc. Thus, the figure E61 is a figure having an emphasis degree in accordance with the total time Tc. The control unit 47 stores the feature quantity, the total time, and the emphasis degree of the region of interest R7 are stored in the region-of-interest storage unit 50 in association with the region of interest R7.

Subsequently, as illustrated in FIG. 11, no region of interest is detected in the frame images 38a at time t+1 and time t+2.

When the time further elapses, as illustrated in FIG. 11, the region-of-interest detecting unit 41 detects a region of interest in the frame image 38a at time t+3. Herein, an elapsed time Tp=(t+3)−t=3 from the time t at the last detection of the region of interest R7 until time t+3 is less than the certain time Tk.

The identical-region-of-interest determining unit 46 compares the feature quantity of the region of interest R7 stored in the region-of-interest storage unit 50 and the feature quantity of the region of interest detected in the frame image 38a at time t+3 and determines whether the region of interest is identical. Herein, it is determined that the region of interest is identical.

For the region of interest R7 detected in the frame image 38a at time t+3, the emphasis-degree setting unit 45 takes over the total time and the emphasis degree of the region of interest R7 stored in the region-of-interest storage unit 50 and adds, to the total time, the elapsed time Tp from time t until time t+3. That is, as the total time, time measurement starts at the timing of emphasis of the region of interest, and the measured time includes the time during which the region of interest is not emphasized.

Thus, the total time of the region of interest R7 is Tc+Tp, and the emphasis degree is an emphasis degree in accordance with the total time Tc+Tp. As illustrated in FIG. 11, a figure E62 is superposed on the frame image 38a at time t+3. The figure E62 is a frame-shaped figure that surrounds the region of interest R7 and has an emphasis degree in accordance with Tc+Tp.

If the time during which no region of interest is detected exceeds the certain time Tk, the feature quantity, the total time, and the emphasis degree of the region of interest stored in the region-of-interest storage unit 50 are reset (deleted). The certain time Tk during which information on the region of interest is continuously held may be a predetermined fixed value or may be determined from the amount of unevenness between the detected region of interest and its periphery, the color difference between the detected region of interest and its periphery, or the like. Alternatively, a user may set a desired value.

Herein, the elapsed time Tp added to the total time Tc that is taken over includes the time during which detection of the region of interest is stopped. However, only the time during which the region of interest is actually detected may be added. That is, time measurement may start at the timing of emphasis of the region of interest, and the total time may be a time measured excluding the time during which the region of interest is not emphasized. For example, the total time at time t+3 may be Tc+1 excluding time t+1 and time t+2 during which the region of interest R7 is not detected. In this case, the time at the last detection of the region of interest R7 is stored in the region-of-interest storage unit 50, and thus, the time during which the region of interest R7 is not detected can be recognized.

In addition, herein, upon detection of a region of interest in the frame image 38a at time t+3, it is determined whether the region of interest is identical with the region of interest R7 in the frame image 38a at the last-detection time t. If it is determined that the region of interest is not identical with the region of interest R7 in this determination, it may be determined whether the region of interest is identical with a third region of interest, which is a region of interest in a frame image 38a (an example of a third medical image) preceding (e.g., at time t−1) the frame image 38a at time t in time series.

As a result, if it is determined that the region of interest is identical, the emphasis-degree setting unit 45 may take over the total time and the emphasis degree of the third region of interest stored in the region-of-interest storage unit 50 for the region of interest detected in the frame image 38a at time t+3, and may add, to the total time, the elapsed time Tp from time t−1 until time t+3, for example.

Emphasis on Plurality of Regions of Interest

In a case in which a plurality of regions of interest are detected in a moving image that is being observed, if a user pays too much attention to one region of interest, the user may divert attention from the existence of another region of interest. In particular, in a case in which the regions of interest are away from each other or each region of interest exists at an end of the screen, for example, the user is likely to divert attention from a region of interest, which may result in missing of the region of interest. In addition, in a case in which the endoscope 10 is operated quickly, even if a plurality of regions of interest are detected, a region of interest may become out of the screen before its emphasis degree becomes high, and the user may not pay attention to it. Thus, in a case in which a plurality of regions of interest are detected, for example, their emphasis degrees may be increased, or increasing rates of the emphasis degrees may be increased, so as to avoid this problem.

Figure 12:
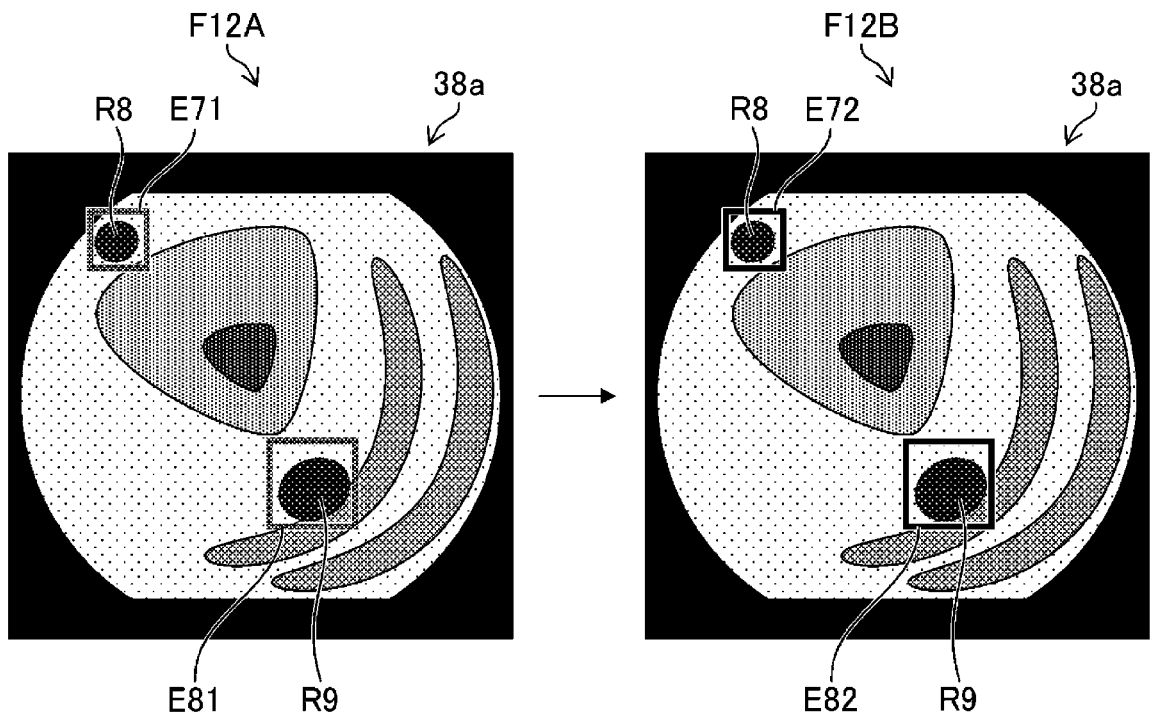
FIG. 12 illustrates an example of change of figures when a plurality of regions of interest are detected.

FIG. 12 illustrates an example of change of figures when a plurality of regions of interest are detected in a single medical image. F12A illustrated in FIG. 12 illustrates a frame image 38a on which a figure E71 that surrounds a region of interest R8 and a figure E81 that surrounds a region of interest R9 are superposed. In addition, F12B illustrated in FIG. 12 illustrates a frame image 38a on which a figure E72 that surrounds the region of interest R8 and a figure E82 that surrounds the region of interest R9 are superposed. The frame image 38a illustrated in F12B is a frame image subsequent to the frame image 38a illustrated in F12A in time series.

As in the above case, the emphasis degree of the figure E72 is set to a relatively larger value than that of the figure E71. In addition, the emphasis degree of the figure E82 is set to a relatively larger value than that of the figure E81. Furthermore, herein, the minimum, the maximum, and the increasing rate of the emphasis degree are set to larger values as the number of regions of interest increases.

Figure 13:
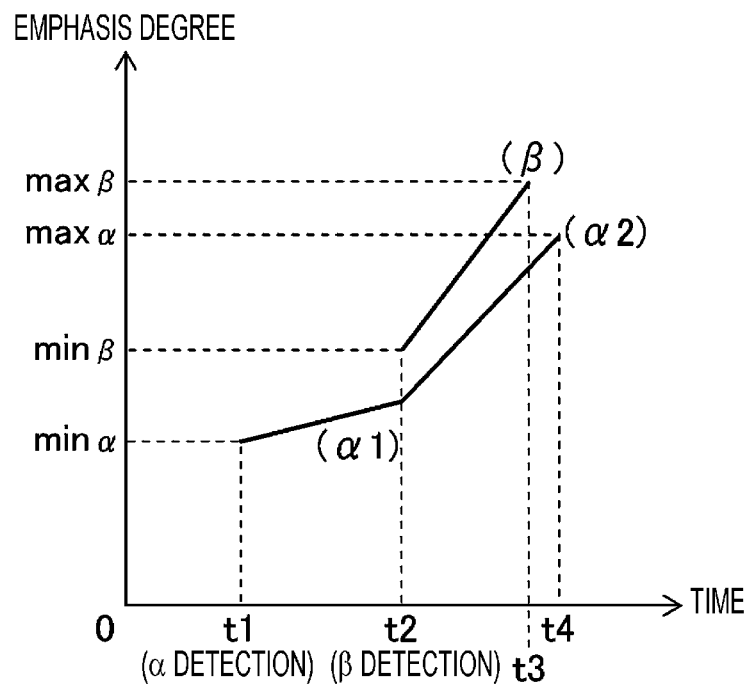
FIG. 13 is a graph illustrating change of emphasis degrees in the example illustrated in FIG. 12.

FIG. 13 is a graph illustrating an example of change of emphasis degrees when two regions of interest are detected, in which the horizontal axis represents time and the vertical axis represents emphasis degree. As illustrated in FIG. 13, a first region of interest is emphasized by using a minimum min $\alpha$, a maximum max $\alpha$, and an increasing rate R$\alpha$1. In addition, a second region of interest is emphasized by using a minimum min $\beta$, a maximum max $\beta$, and an increasing rate R$\beta$. Herein, min $\alpha$, min $\beta$, max $\alpha$, max $\beta$, R$\alpha$1, and R$\beta$ have relationships min $\alpha$<min $\beta$, max $\alpha$<max $\beta$, and R$\alpha$1<R$\beta$. These minimums, maximums, and increasing rates are stored in advance in the storage unit 49.

The emphasis degrees of the regions of interest illustrated in FIG. 12 change as illustrated in FIG. 13. Herein, the first region of interest R8 is detected at time t1, and the region of interest R9 is detected at time t2 subsequent to time t1. In this case, for the region of interest R8, the emphasis-degree setting unit 45 sets the emphasis degree being the minimum min $\alpha$ at time t1 and then sets the emphasis degree that is a value increased at the increasing rate R$\alpha$1 with respect to the total time.

Subsequently, the second region of interest R9 is detected at time t2. For the region of interest R9, the emphasis-degree setting unit 45 sets the emphasis degree being the minimum min $\beta$ at time t2 and then sets the emphasis degree that is a value increased at the increasing rate R$\beta$ with respect to the total time. In addition, from time t2, the emphasis-degree setting unit 45 sets the emphasis degree of the region of interest R8 to a value increased at the increasing rate R$\alpha$2. The increasing rate R$\alpha$2 has a relationship R$\alpha$1<R$\alpha$2<R$\beta$.

When the time further elapses, at time t3, the emphasis-degree setting unit 45 sets the emphasis degree of the region of interest R9 to the maximum max $\beta$. Subsequently, emphasis on the region of interest R9 ends. Note that emphasis at the emphasis degree being the maximum max $\beta$ may be maintained. In addition, at time t4, the emphasis-degree setting unit 45 sets the emphasis degree of the region of interest R8 to the maximum max $\alpha$. Subsequently, as in the case for the region of interest R9, emphasis on the region of interest R8 ends. Note that emphasis at the emphasis degree being the maximum max $\alpha$ may be maintained.

Herein, the minimum, the maximum, and the increasing rate of the emphasis degree are set to larger values as the number of regions of interest increases. However, at least one of the minimum, the maximum, or the increasing rate of the emphasis degree may be set to a larger value. In this manner, by setting at least one of the minimum or the maximum of the emphasis degree to a larger value as the number of regions of interest increases and increasing the emphasis degree, the user can pay attention to the regions of interest, and the user can be prevented from missing the regions of interest. In addition, by setting the increasing rate of the emphasis degree to a larger value as the number of regions of interest increases and increasing the emphasis degree at an earlier stage, the user can pay attention to the regions of interest, and the user can be prevented from missing the regions of interest.

Setting of Emphasis Degree in Accordance with Position in Image

In order to reduce a load on a patient, an endoscopic inspection needs to be performed quickly, without taking time. In addition, operation of the endoscope 10 is complex. Thus, the insertion part 20 may be moved too quickly in some cases.

In a case in which the insertion part 20 is moved quickly, when a region of interest is detected at a portion where a user does not pay attention, the user may miss the region of interest. In particular, in a case in which the region of interest is detected at an end portion of the image, the user is likely to miss the region of interest.

In order to prevent such missing, the minimum, the maximum, and the increasing rate may be set in accordance with the distance from the center of the image.

Figure 14:
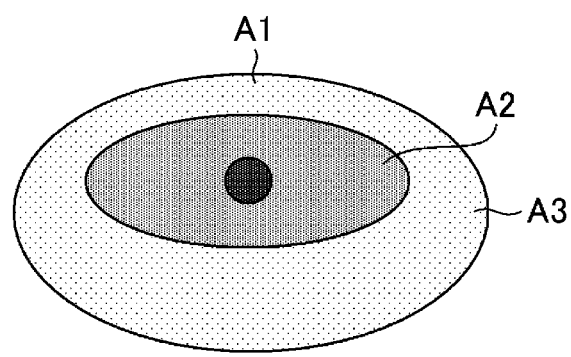
FIG. 14 is a drawing for explaining a visual performance.

FIG. 14 is a drawing for explaining a human visual performance. A region A1 illustrated in FIG. 14 is a region including a focus point with the highest eyesight. A region A2 is a region where information can be received instantly with only an eye movement from the focus point. A region A3 is a region where information can be received without effort with an eye movement and a head movement from the focus point.

As the human visual performance, the eyesight is highest at the focus point and suddenly decreases to a vague view as the distance from the focus point increases. Typically, since a user often focuses on the center of an image, it is preferable to increase a supporting function at an end portion of the image. The above trend differs in an upper portion, a lower portion, a left portion, and a right portion, and thus, the increasing rate may be changed in accordance with the direction. For example, support is more needed in the upper direction than in the other directions, and thus, at least one of the minimum, the maximum, or the increasing rate is preferably made relatively larger.

Setting of Emphasis Degree in Accordance with Brightness

The minimum, the maximum, and the increasing rate of the emphasis degree may be set based on luminance of the region of interest or a difference between the luminance of the region of interest and luminance of a region outside the region of interest. As the region of interest is darker, or as the difference in brightness from the periphery is smaller, the user is more likely to miss the region of interest. Thus, in this case, at least one of the minimum, the maximum, or the increasing rate of the emphasis degree is set to a relatively large value.

Conversely, as the region of interest is brighter, or as the difference in brightness from the periphery is larger, the user is more unlikely to miss the region of interest. Thus, at least one of the minimum, the maximum, or the increasing rate of the emphasis degree is set to a relatively small value in order to prioritize the visibility of the image.

Figure 15:
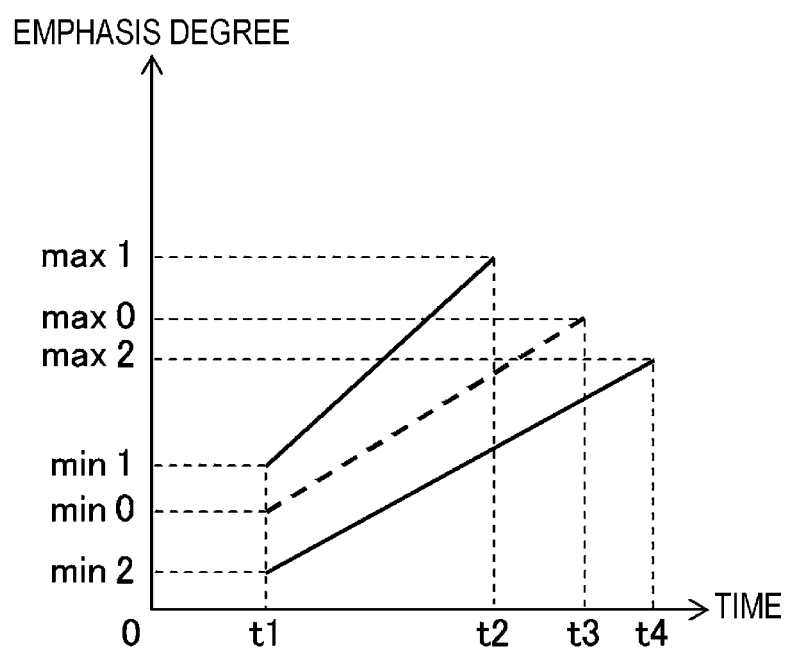
FIG. 15 is a graph illustrating change of an emphasis degree in accordance with luminance of a region of interest.

FIG. 15 is a graph illustrating an example of change of the emphasis degree in accordance with brightness of the region of interest, in which the horizontal axis represents time and the vertical axis represents emphasis degree. In a case in which the brightness of the region of interest is normal, the minimum of the emphasis degree is min0, and the maximum thereof is max0. In addition, as illustrated in FIG. 15, an increasing rate Ri0 is $Ri0=(max0-min0)/(t3-t1)$.

In a case in which the brightness of the region of interest is relatively dark, the minimum of the emphasis degree is min1, and the maximum thereof is max1. In addition, as illustrated in FIG. 15, an increasing rate Ri1 is $Ri1=(max1-min1)/(t2-t1)$. Herein, min0, min1, max0, max1, Ri0, and Ri1 have relationships $min0<min1$, $max0<max1$, and $Ri0<Ri1$.

In a case in which the brightness of the region of interest is relatively bright, the minimum of the emphasis degree is min2, and the maximum thereof is max2. In addition, as illustrated in FIG. 15, an increasing rate Ri2 is $Ri2=(max2-min2)/(t4-t1)$. Herein, min0, min2, max0, max2, Ri0, and Ri2 have a relationship $min0>min2$, $max0>max2$, and $Ri0>Ri2$. These minimums, maximums, and increasing rates are stored in advance in the storage unit 49.

The brightness of the region of interest can be acquired from the luminance of the region of interest. Herein, change of the emphasis degree in accordance with the luminance of the region of interest is illustrated. However, the same applies to a case in which the difference between the luminance of the region of interest and the luminance of the region outside the region of interest is used.

Setting of Emphasis Degree in Accordance with Color Information

As in a case of setting the emphasis degree in accordance with the brightness, the minimum, the maximum, and the increasing rate of the emphasis degree may be set based on color information of the region of interest or a difference between the color information of the region of interest and color information of a region outside the region of interest.

As the saturation of the region of interest is lower, as the color difference from the periphery is smaller, or as the color difference from the color of a figure to be used as reporting information is smaller, the user is more likely to miss the region of interest. Thus, as in the case of brightness, at least one of the minimum, the maximum, or the increasing rate of the emphasis degree is set to a relatively large value. For example, as illustrated in FIG. 15, the minimum of the emphasis degree is min1, the maximum thereof is max1, and the increasing rate thereof is Ri1.

Conversely, as the saturation of the region of interest is higher, as the color difference from the periphery is larger, or as the color difference from the color of a figure is larger, the user is more unlikely to miss the region of interest. Thus, at least one of the minimum, the maximum, or the increasing rate of the emphasis degree is set to a relatively small value in order to prioritize the visibility of the image. For example, as illustrated in FIG. 15, the minimum of the emphasis degree is min2, the maximum thereof is max2, and the increasing rate thereof is Ri2.

The color information is not limited to the RGB (Red, Green, Blue) color space. For example, the color information may also be the device-independent Lab color space of the L*a*b* color system, the YMCK (Cyan, Magenta, Yellow, blacK) color space of a color system suitable for printing processing, the HLS (Hue-Luminance-Saturation) color space, the so-called YCbCr (Y: luminance, CbCr: color difference) color space formed of luminance and color difference, or the like.

The color difference may also be determined whether the color difference falls within the allowable range (JIS standard or typically used by various industrial associations) distinguishable by humans.

Setting of Emphasis Degree in Accordance with Movement Information

As in cases of brightness and color information, the minimum, the maximum, and the increasing rate of the emphasis degree may be set based on movement information such as a movement amount, a movement direction, or the like of the region of interest.

As the movement amount of the region of interest is larger, it is more necessary for the user to be conscious about detection at an earlier stage. In addition, in a case in which the movement direction of the region of interest is toward an end portion of the image, the user is likely to miss the region of interest. Thus, at least one of the minimum, the maximum, or the increasing rate of the emphasis degree is set to a relatively large value.

Conversely, in a case in which the movement amount of the region of interest is small, it is unnecessary to be conscious at an early stage. In addition, in a case in which the movement direction of the region of interest is toward the center of the image, the user is unlikely to miss the region of interest. Thus, at least one of the minimum, the maximum, or the increasing rate of the emphasis degree is set to a relatively small value.

Region of Interest that is Not Identical but Exists on the Periphery

In some cases, even if a region of interest is identical, the shape thereof in a captured image may differ depending on the insertion angle of the insertion part 20, for example. In addition, in some cases, the region-of-interest detecting unit 41 cannot detect a region of interest as an identical region of interest with an accuracy of 100%. For such a reason, although a region of interest is identical, if it is not determined that the region of interest is an identical region of interest, emphasis processing with the minimum emphasis degree is continuously performed in each frame image. Such a situation interrupts a user's attention, which is not preferable.

Thus, even if it is not determined that a detected region of interest is identical with a previously detected region of interest, in a case in which the detected region of interest exists in a certain area, the total time and the emphasis degree of the previously detected region of interest may be taken over. Even if the shape or the like differs, reaction of the region-of-interest detecting unit 41 indicates a high likelihood of the region of interest on the periphery, and the user is made to focus it, which is useful in preventing the user from missing the region of interest.

Figure 16:
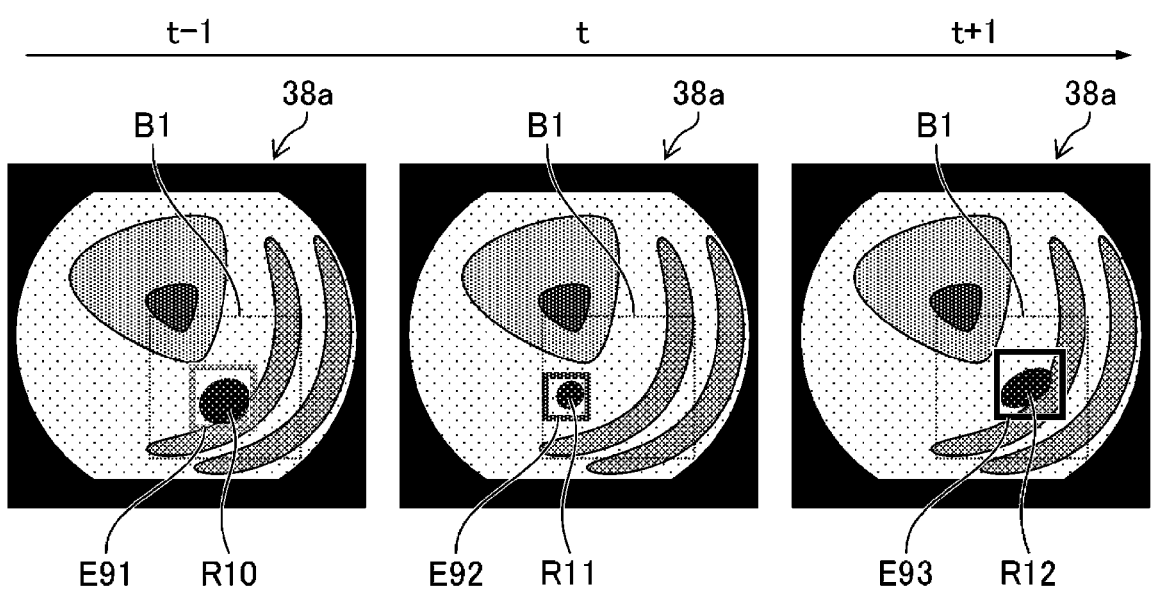
FIG. 16 is a drawing for explaining a region of interest that is not identical but exists on the periphery.

FIG. 16 is a drawing for explaining a region of interest that is not identical but exists on the periphery. FIG. 16 illustrates examples of frame images 38a at time t−1, time t, and time t+1. These frame images are continuous in the moving image 38.

In the frame image 38a at time t−1, a region of interest R10 is detected. A figure E91 at an emphasis degree in accordance with the total time of the region of interest R10 is superposed at the position of the region of interest R10 on the frame image 38a. The feature quantity, the total time, and the emphasis degree of the region of interest R10 are stored in the region-of-interest storage unit 50 in association with the region of interest R10.

Herein, for the region of interest R10, the region-of-interest detecting unit 41 sets a certain area B1 centered at the region of interest R10. Although the frame shape indicating the area B1 is illustrated in each frame 38a for explanation in FIG. 16, the frame shape indicating the area B1 is not displayed on the display 16.

Subsequently, upon the frame image 38a at time t being input to the region-of-interest detecting unit 41, the region-of-interest detecting unit 41 detects a region of interest R11 from the frame image 38a. In addition, the region-of-interest information acquiring unit 42 acquires the feature quantity of the region of interest R11.

Subsequently, the identical-region-of-interest determining unit 46 compares the feature quantity of the region of interest R10 stored in the region-of-interest storage unit 50 and the feature quantity of the region of interest R11 calculated by the region-of-interest information acquiring unit 42 with each other, and determines whether the region of interest R10 and the region of interest R11 are identical regions of interest. Herein, the feature quantities are different, and the identical-region-of-interest determining unit 46 determines that the regions of interest are not identical.

Upon determination that the regions of interest are not identical, the identical-region-of-interest determining unit 46 further determines whether the position of the region of interest R11 in the frame image 38a is a position within the area B1 set for the region of interest R10. Herein, the identical-region-of-interest determining unit 46 determines that the position of the region of interest R11 is a position within the area B1.

Upon determination that the position of the region of interest R11 is a position within the area B1, the total-time measuring unit 44 measures the total time of the region of interest R11 by taking over the total time of the region of interest R10 stored in the region-of-interest storage unit 50.

In addition, in accordance with the total time measured by taking over the total time of the region of interest R10, the emphasis-degree setting unit 45 sets the emphasis degree of the region of interest R11. The emphasis-degree setting unit 45 may alternatively calculate and set the emphasis degree of the region of interest R11 from the emphasis degree of the region of interest R10 stored in the region-of-interest storage unit 50, the elapsed time from time t−1 until time t, and the predetermined increasing rate of the emphasis degree.

As a result, as illustrated in FIG. 16, on the frame image 38a at time t, a frame-shaped figure E92 that emphasizes the region of interest R11 is superposed at the position of the region of interest R11. The figure E92 is a figure having a relatively larger emphasis degree than the figure E91 for the time that equals to one frame. In this manner, the region of interest R11 can take over the emphasis degree of the region of interest R10.

In addition, the control unit 47 stores the feature quantity, the total time, and the emphasis degree of the region of interest R11 in the region-of-interest storage unit 50 in association with the region of interest R11.

Subsequently, upon the frame image 38a at time t+1 being input to the region-of-interest detecting unit 41, the region-of-interest detecting unit 41 detects a region of interest R12 from the frame image 38a. In addition, the region-of-interest information acquiring unit 42 calculates the feature quantity of the region of interest R12.

Subsequently, the identical-region-of-interest determining unit 46 compares the feature quantity of the region of interest R11 stored in the region-of-interest storage unit 50 and the feature quantity of the region of interest R12 calculated by the region-of-interest information acquiring unit 42 with each other, and determines whether the region of interest R11 and the region of interest R12 are identical regions of interest. Herein, the feature quantities are different, and the identical-region-of-interest determining unit 46 determines that the regions of interest are not identical.

The identical-region-of-interest determining unit 46 further determines whether the position of the region of interest R12 in the frame image 38a is a position within the area B1 set for the region of interest R10. Herein, the identical-region-of-interest determining unit 46 determines that the position of the region of interest R12 is a position within the area B1.

Upon determination that the position of the region of interest R12 is a position within the area B1, the total-time measuring unit 44 measures the total time of the region of interest R12 by taking over the total time of the region of interest R11 stored in the region-of-interest storage unit 50.

In addition, in accordance with the total time measured by taking over the total time of the region of interest R11, the emphasis-degree setting unit 45 sets the emphasis degree of the region of interest R12.

As a result, as illustrated in FIG. 16, on the frame image 38a at time t+1, a frame-shaped figure E93 that emphasizes the region of interest R12 is superposed at the position of the region of interest R12. The figure E93 is a figure having a relatively larger emphasis degree than the figure E92 for the time that equals to one frame. In this manner, the region of interest R12 can take over the emphasis degree of the region of interest R11.

Note that, if it is determined that the position of the region of interest R12 is not a position within the area B1, the region of interest R12 is treated as a newly detected region of interest. That is, the total-time measuring unit 44 newly starts to measure the total time of the region of interest R12, and the emphasis-degree setting unit 45 sets the emphasis degree of the region of interest R12 to the predetermined minimum.

Herein, the identical-region-of-interest determining unit 46 determines whether the position of the region of interest R12 in the frame image 38a is a position within the area B1 set for the initially detected region of interest R10. However, a new area may be set for the region of interest R11, and it may be determined whether the region of interest R12 is at a position within the area set for the region of interest R11.

In addition, the identical-region-of-interest determining unit 46 sets the certain area B1 centered at the region of interest R10. However, the area used for determination of the identical-region-of-interest determining unit 46 in order to take over the emphasis degree may be a preset fixed area.

In the above manner, even if it is not determined that a detected region of interest is identical with a previously detected region of interest, in a case in which the detected region of interest exists in a certain area, by taking over the emphasis degree of the previously detected region of interest, the region of interest can be emphasized at an appropriate emphasis degree.

Case in which Plurality of Display Units Exist

Although an example of displaying the moving image 38 on a single display unit has been described above, the medical image processing apparatus 14 may include a plurality of display units. Some users do not wish the reporting information to be superposed on an image that is being observed. Thus, an image on which the reporting information is superposed may be displayed on a display unit that is different from a display unit that displays an image that is being observed.

Figure 17:
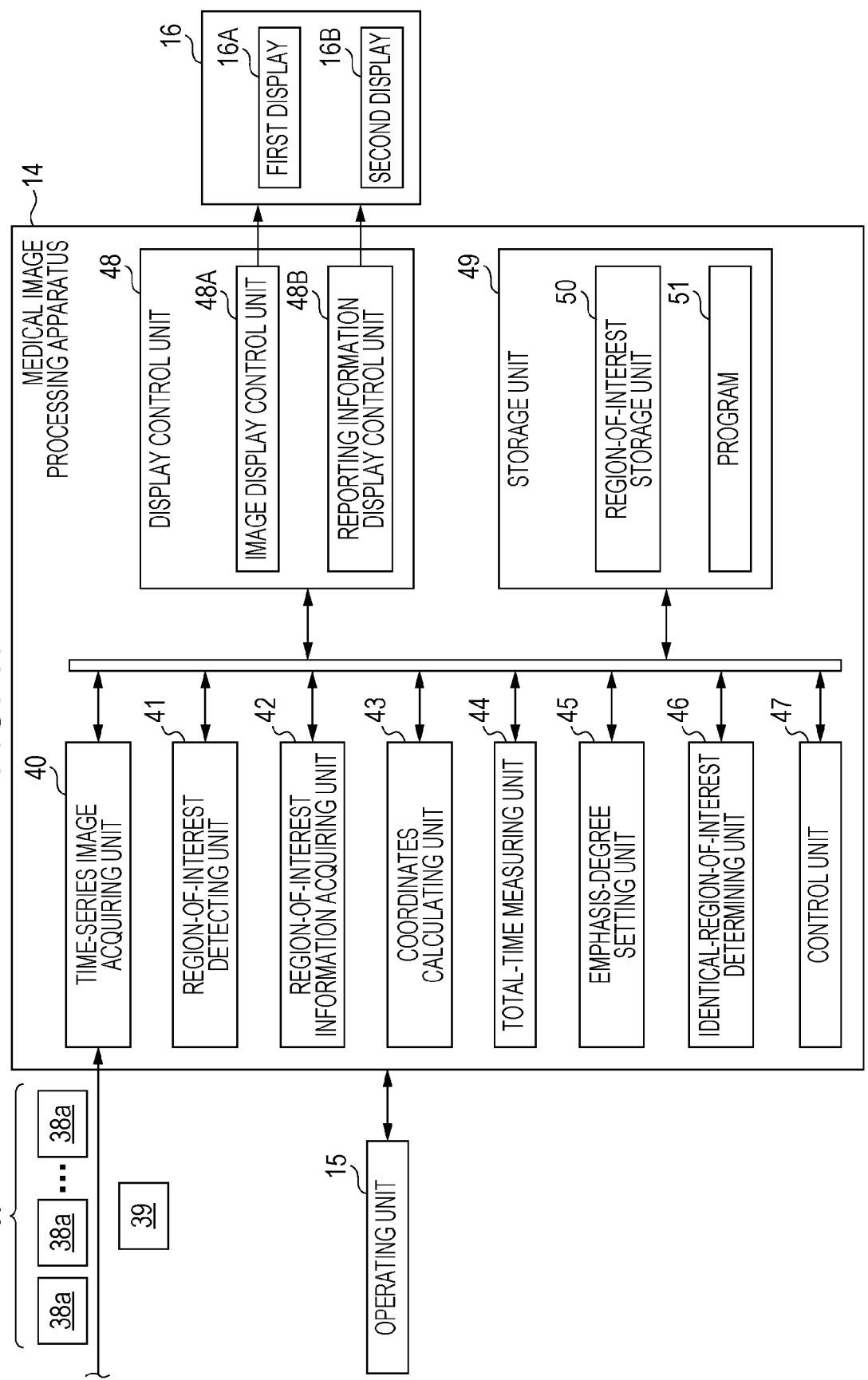
FIG. 17 is a block diagram illustrating an electric configuration of the medical image processing apparatus including a plurality of display units.

FIG. 17 is a block diagram illustrating an electric configuration of the medical image processing apparatus 14 including a plurality of display units. The display 16 includes a first display unit 16A and a second display unit 16B. The first display unit 16A and the second display unit 16B may be two different monitors or may be different regions of one monitor.

The image display control unit 48A outputs a moving image 38 acquired by the time-series image acquiring unit 40 to at least one of the first display unit 16A or the second display unit 16B. In addition, the reporting information display control unit 48B outputs reporting information for reporting a region of interest to at least one of the first display unit 16A or the second display unit 16B.

Figure 18:
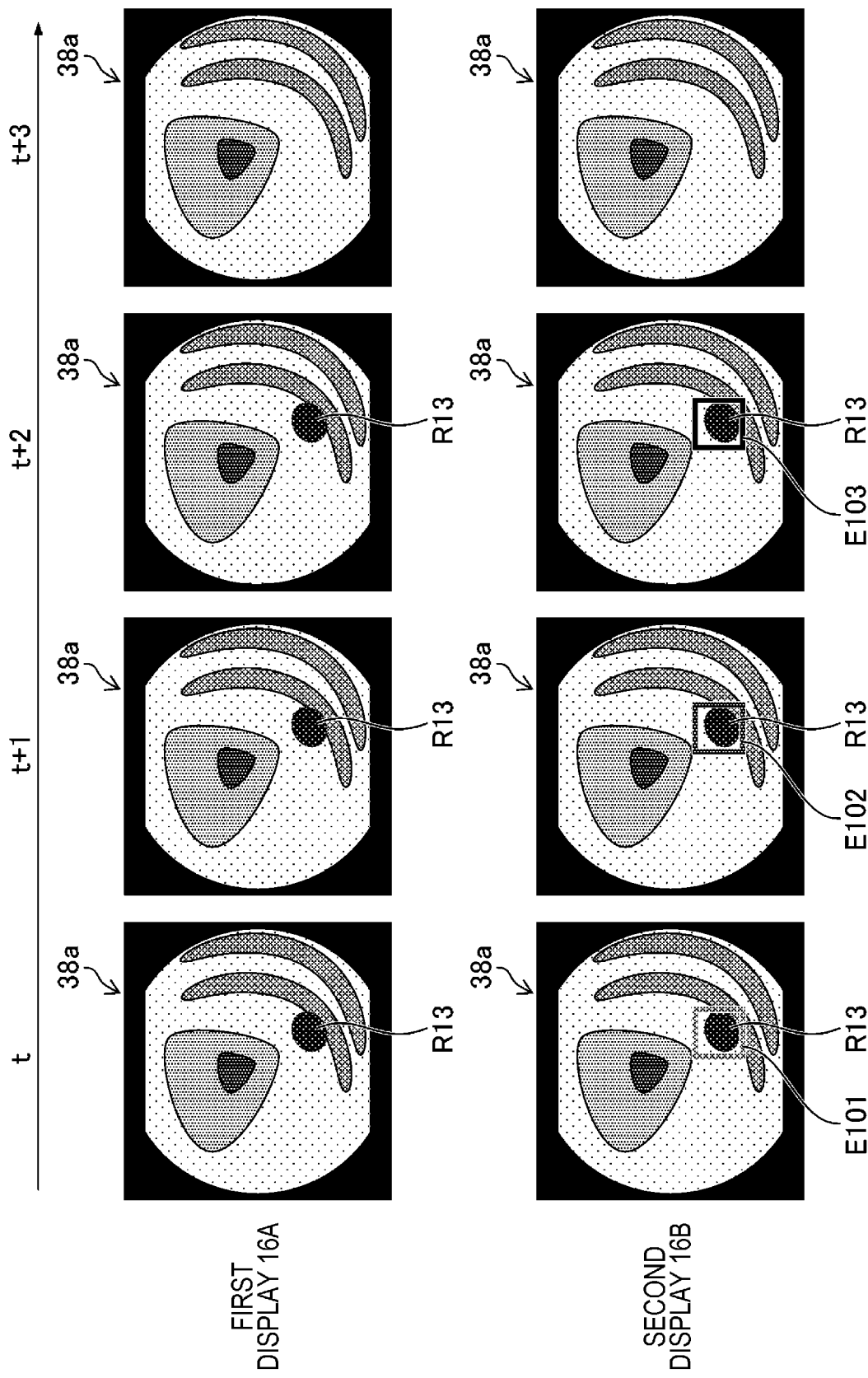
FIG. 18 is a drawing for explaining display content on the plurality of display units.
Figure 19:
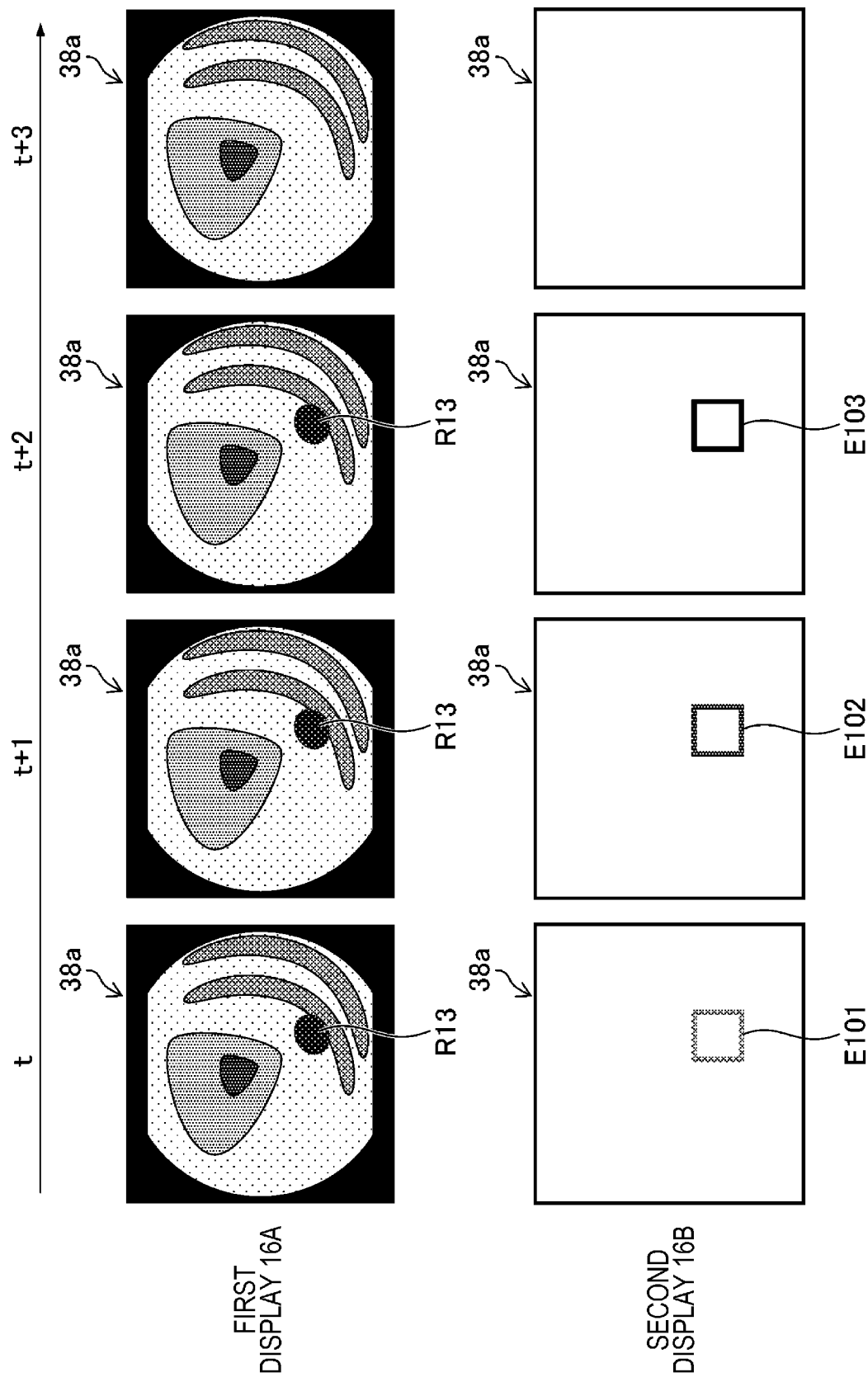
FIG. 19 is a drawing for explaining display content on the plurality of display units.
Figure 20:
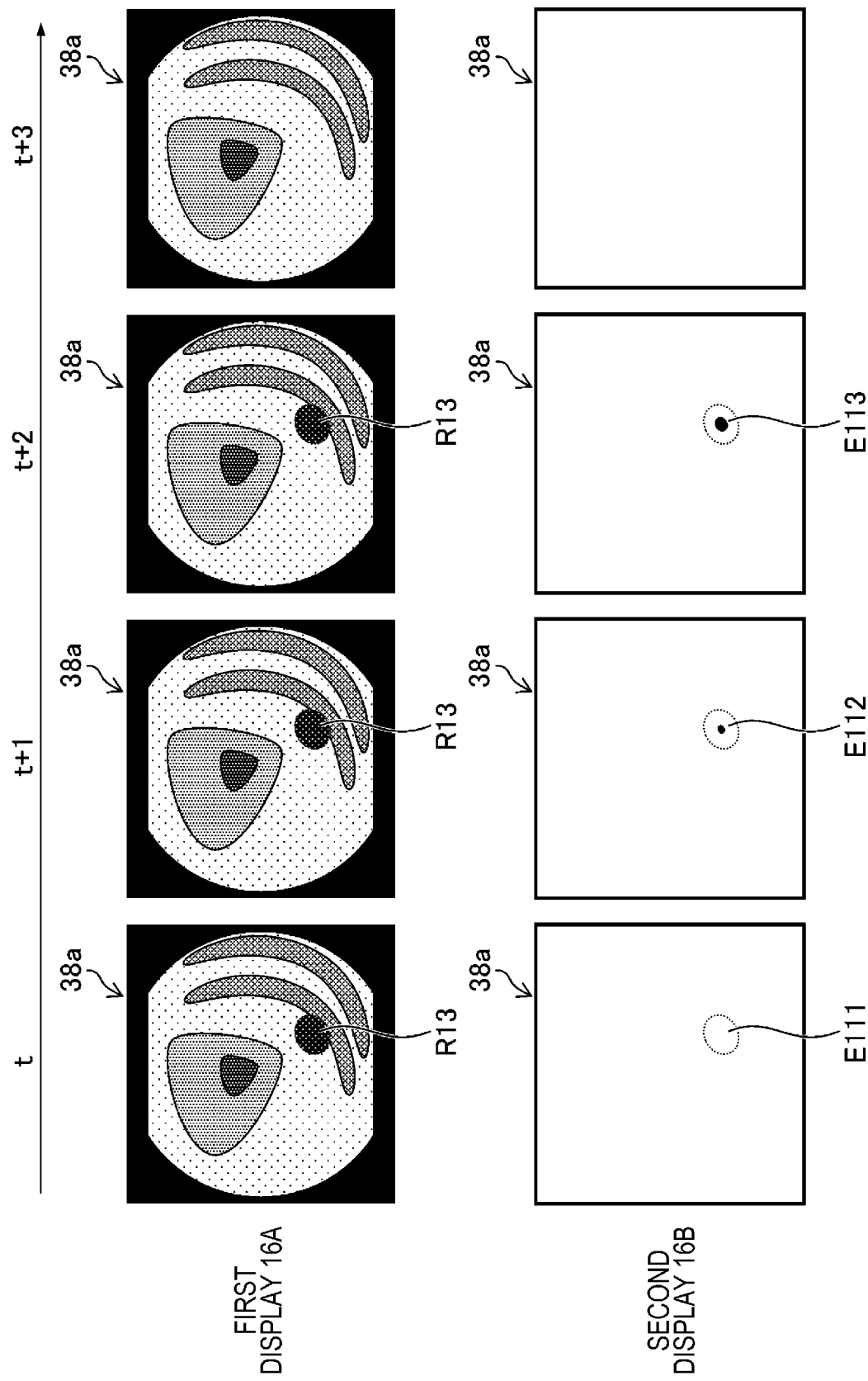
FIG. 20 is a drawing for explaining display content on the plurality of display units.

Each of FIG. 18 to FIG. 20 is a drawing for explaining display content on the plurality of display units. Upper portions of FIG. 18 to FIG. 20 illustrate examples of display content at time t, time t+1, time t+2, and time t+3 on the first display unit 16A, and lower portions of FIG. 18 to FIG. 20 illustrate examples of display content at time t, time t+1, time t+2, and time t+3 on the second display unit 16B.

As illustrated in FIG. 18 to FIG. 20, frame images 38a at time t, time t+1, time t+2, and time t+3, which are continuous frame images in the moving image 38, are displayed on the first display unit 16A at time t, time t+1, time t+2, and time t+3, respectively. The frame images 38a at time t, time t+1, and time t+2 include an identical region of interest R13. In addition, the frame image 38a at time t+3 does not include a region of interest.

In the example illustrated in FIG. 18, as in the first display unit 16A, frame images 38a at time t, time t+1, time t+2, and time t+3 are displayed on the second display unit 16B, at time t, time t+1, time t+2, and time t+3, respectively.

In addition, on the frame images 38a at time t, time t+1, and time t+2 displayed on the second display unit 16B, a figure E101, a figure E102, and a figure E103 are respectively superposed at the position of the region of interest R13. The figure E101, the figure E102, and the figure E103 have emphasis degrees in accordance with total times of the region of interest R13. The figure E101, the figure E102, and the figure E103 are frame-shaped figures that surround the position of the region of interest R13 and have different line transmittances.

By displaying the moving image 38 in this manner, a user can observe the image on the first display unit 16A and can check reports of a region of interest on the second display unit 16B as necessary.

In addition, in the example illustrated in FIG. 19, frame images 38a are not displayed on the second display unit 16B, and only figures that are reporting information are displayed. The second display unit 16B displays the figure E101, the figure E102, and the figure E103 having emphasis degrees in accordance with total times of the region of interest R13 at time t, time t+1, and time t+2, respectively, at the position corresponding to the position of the region of interest R13 in each frame image 38a. In addition, no figure is displayed at time t+3.

In addition, also in the example illustrated in FIG. 20, only figures that are reporting information are displayed on the second display unit 16B. The second display unit 16B displays a figure E111, a figure E112, and a figure E113 having emphasis degrees in accordance with total times of the region of interest R13 at time t, time t+1, and time t+2, respectively, at the position corresponding to the position of the region of interest R13 in each frame image 38a. The figure E111, the figure E112, and the figure E113 are figures having substantially the same shape as the region of interest R13 and different transmittances. In addition, no figure is displayed at time t+3.

Also in a case of such display, a user can observe the image on the first display unit 16A and can check reports of a region of interest on the second display unit 16B as necessary.

Medical Image Processing Method: Second Embodiment

Figure 21:
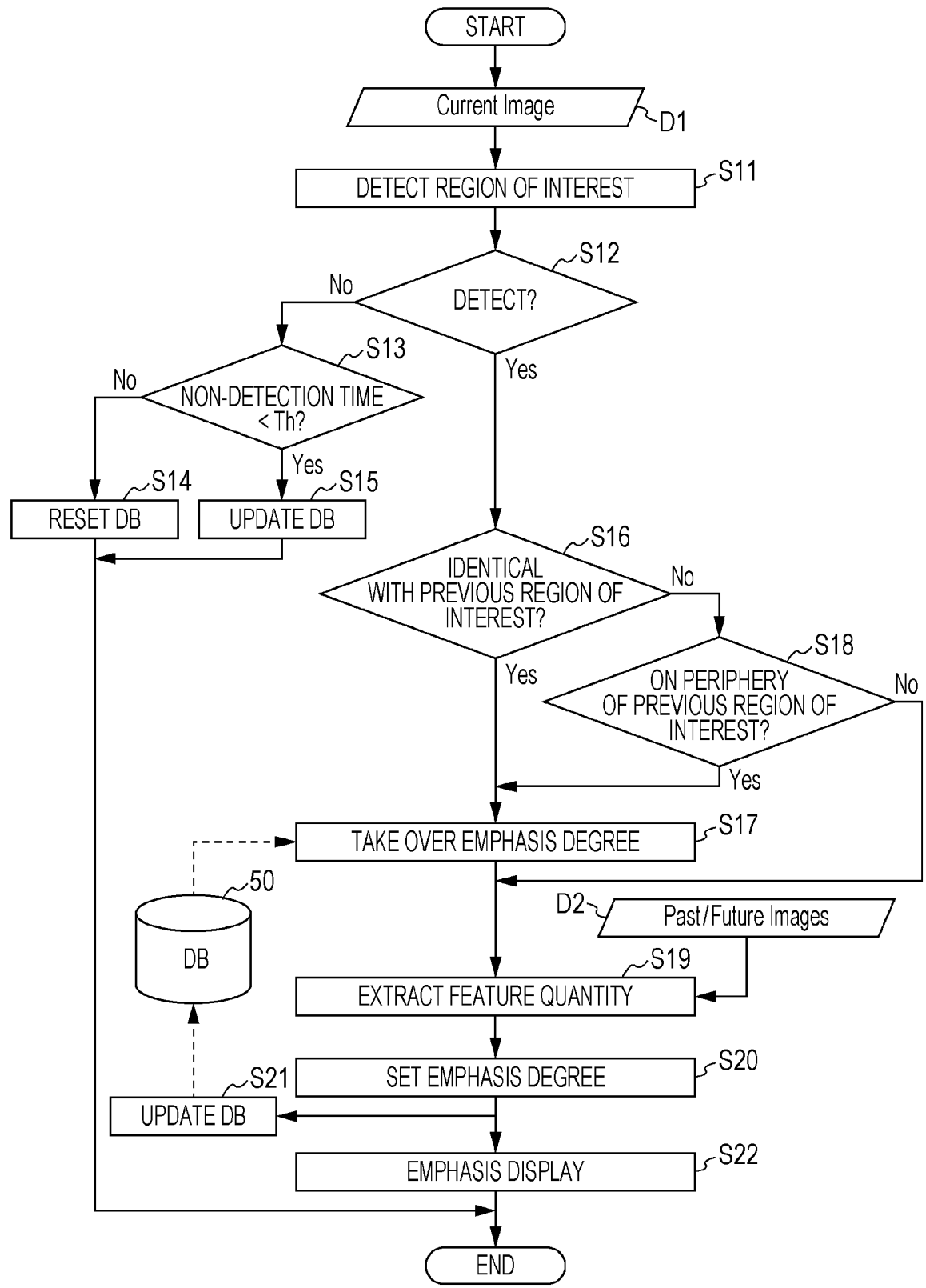
FIG. 21 is a flowchart illustrating an example of each process of the medical image processing method according to the second embodiment.

Another example of a medical image processing method according to a second embodiment will be described. FIG. 21 is a flowchart illustrating an example of each process of the medical image processing method according to the second embodiment.

In step S11, the time-series image acquiring unit 40 acquires, as data D1, a frame image 38a in a moving image 38 captured by the endoscope 10. The region-of-interest detecting unit 41 detects a region of interest from the data D1.

In step S12, the control unit 47 determines whether the region-of-interest detecting unit 41 has detected a region of interest.

If the region-of-interest detecting unit 41 has not detected a region of interest, the process proceeds to step S13. In step S13, the control unit 47 further determines whether a continuous non-detection time during which no region of interest is detected is less than a threshold time Th. Although the continuous non-detection time is determined herein, the number of continuous non-detection frames may alternatively be determined. Further alternatively, a total non-detection time, or a total number of continuous non-detection frames may be determined.

If the continuous non-detection time is greater than or equal to the threshold time Th, the process proceeds to step S14, and the control unit 47 resets the region-of-interest storage unit 50, which is a database. That is, the feature quantity, the total time, and the emphasis degree of the region of interest stored in the region-of-interest storage unit 50 are deleted. By deleting the feature quantity, the total time, and the emphasis degree of the region of interest, if the next region of interest is detected, it may be determined that the region of interest is a newly detected region of interest.

If the continuous non-detection time is less than the threshold time Th, the process proceeds to step S15, and the control unit 47 updates the region-of-interest storage unit 50, which is a database. That is, the feature quantity, the total time, and the emphasis degree of the region of interest stored in the region-of-interest storage unit 50 are updated to most recent states. The continuous non-detection time is also updated. By updating the region-of-interest storage unit 50 in the above manner, even if detection of the region of interest is stopped, in a case in which the identical region of interest is detected again, the emphasis degree and the like can be taken over. In addition, determination of the continuous non-detection time can be performed appropriately.

When resetting the region-of-interest storage unit 50 in step S14 or updating the region-of-interest storage unit 50 in step S15 ends, the process in this flowchart ends.

On the other hand, if it is determined in step S12 that the region-of-interest detecting unit 41 has detected a region of interest, the process proceeds to step S16.

In step S16, the identical-region-of-interest determining unit 46 determines whether the region of interest detected by the region-of-interest detecting unit 41 is identical with a region of interest detected in a past frame image. This determination is performed by comparing the feature quantity of the previous region of interest stored in the region-of-interest storage unit 50 and the feature quantity of the region of interest detected in step S11, the feature quantity being calculated by the region-of-interest information acquiring unit 42, with each other.

If it is determined in step S16 that the regions of interest are identical, the process proceeds to step S17. If it is determined in step S16 that the regions of interest are not identical, the process proceeds to step S18.

In step S18, the identical-region-of-interest determining unit 46 further determines whether the position of the region of interest detected in step S11 in the image is a position on the periphery of the previously detected region of interest. The position on the periphery is a position within a certain area centered at a previously detected region of interest, for example.

If it is determined in step S18 that the region of interest exists at the position on the periphery of the previously detected region of interest, the process proceeds to step S17.

In step S17, the total-time measuring unit 44 measures the total time of the region of interest detected in step S11 by taking over the total time of the region of interest stored in the region-of-interest storage unit 50. Thus, the emphasis degree in accordance with the total time can be taken over. Subsequently, the process proceeds to step S19.

In addition, also if it is determined in step S18 that the region of interest does not exist at the position on the periphery of the previously detected region of interest, the process proceeds to step S19.

In step S19, the region-of-interest information acquiring unit 42 acquires, as data D2, a past frame image 38a of the data D1 of the moving image 38, and extracts, from the data D2, feature quantities of the region of interest and of a region outside the region of interest, such as luminance, color, or movement information. The feature quantities may be extracted in all frames, at certain intervals, at timings intended by a user, or the like. If the feature quantities are not extracted, the process may proceed to step S20 from step S17.

Note that the region-of-interest information acquiring unit 42 may acquire, as the data D2, a future frame image 38a of the data D1 of the moving image 38. Although delay occurs if the future frame image 38a is acquired, if movement information is extracted as a feature quantity, by referring to the past frame image 38a and the future frame image 38a, the movement information can be extracted with a high accuracy.

In this regard, as the frame image 38a to be referred to when acquiring the movement information, not only the frame image 38a immediately before or immediately after the current frame image 38a, but also all of any given number of frame images 38a centered at the current frame image 38a or a frame image 38a selected therefrom may be used. This is because the region of interest is not always detected continuously in time series. In addition, regarding the past frame image 38a, targets may be only frame images 38a that take over the emphasis degree.

In step S20, the emphasis-degree setting unit 45 sets the emphasis degree of the region of interest detected in step S11. The emphasis-degree setting unit 45 may set the emphasis degree that is taken over in step S17 as it is or may change the emphasis degree that is taken over in accordance with the feature quantity extracted in step S19 and set the emphasis degree.

In step S21, the feature quantity, the total time, and the emphasis degree of the region of interest are updated in the region-of-interest storage unit 50, which is a database.

Subsequently, in step S22, the image display control unit 48A outputs the frame image 38a that is the data D1 to the display 16. In addition, based on the emphasis degree set by the emphasis-degree setting unit 45, the reporting information display control unit 48B outputs reporting information for reporting the region of interest to the display 16.

Thus, the display 16 displays the frame image 38a in which the region of interest is emphasized.

In the above manner, in a case in which the detected region of interest is identical with the previous region of interest, by taking over the emphasis degree, the region of interest can be emphasized at the emphasis degree of a larger value as the emphasized total time is longer. In addition, even in a case in which the detected region of interest is not identical with the previous region of interest, if the position of the detected region of interest exists on the periphery of the position of the previous region of interest, as in a case in which the regions of interest are identical, by taking over the emphasis degree, the region of interest can be emphasized at the emphasis degree of a larger value as the emphasized total time is longer. In addition, even in a case in which no region of interest is detected, if the non-detection time is less than the threshold time Th, by updating the database, if the identical region of interest is detected again before the threshold time Th elapses, the emphasis degree or the like of the previous region of interest can be taken over.

In the above manner, the region of interest in a medical image can be reported appropriately.

Although an endoscopic image is described as an example of the medical image, the medical image processing apparatus according to this embodiment can be applied to, not only the endoscopic image, but also a time-series medical image such as a capsule endoscopic image or an ultrasound image.

Miscellaneous

It is also possible to constitute a non-transitory recording medium such as a compact disk-read only memory (CD-ROM) storing the program 51 causing a computer to execute the above-described medical image processing method.

Although the endoscope processor apparatus 12 and the medical image processing apparatus 14 are described as different apparatuses from each other in the above embodiments, the endoscope processor apparatus 12 and the medical image processing apparatus 14 may also be constituted as an integrated apparatus, and the functions of the medical image processing apparatus 14 may be provided in the endoscope processor apparatus 12.

In addition, a hardware structure of a processing unit that performs various processes of the endoscope processor apparatus 12 and the medical image processing apparatus 14 is any of the following various processors. Various processors include a central processing unit (CPU) that is a general-purpose processor functioning as various processing units by executing software (programs), a graphics processing unit (GPU) that is a processor specialized in image processing, a programmable logic device (PLD) that is a processor in which the circuit configuration is changeable after manufacture, such as field programmable gate array (FPGA), a dedicated electric circuit that is a processor having a circuit configuration that is specially designed to execute specific processing, such as an application specific integrated circuit (ASIC), and the like.

One processing unit may be constituted by one of these various processors, or may be constituted by two or more processors of the same type or different types (e.g., a combination of a plurality of FPGAs, a combination of a CPU and an FPGA, or a combination of a CPU and a GPU). In addition, a plurality of processing units may be constituted by one processor. As a first example for constituting a plurality of processing units as one processor, one or more CPUs and software may be combined to constitute one processor, and this processor may function as a plurality of processing units, as typified by a computer such as a server or a client. As a second example, a processor may be used that implements the functions of the entire system including a plurality of processing units as one integrated circuit (IC) chip, as typified by a system on chip (SoC) or the like. In this manner, various processing units are constituted by one or more of various processors as a hardware structure.

Furthermore, the hardware structure of these various processors is more specifically electric circuitry obtained by combining circuit elements such as semiconductor elements.

The technical scope of the present invention is not limited to the scope described in the above embodiments, and configurations or the like in each embodiment may be combined as appropriate between the embodiments without departing from the spirit of the present invention.

REFERENCE SIGNS LIST 9 endoscope system
10 endoscope
11 light source apparatus
12 endoscope processor apparatus
13 display apparatus
14 medical image processing apparatus
15 operating unit
16 display
16A first display
16B second display
20 insertion part
21 handheld operating unit
22 universal cord
25 soft part
26 bending part
27 distal end part
28 imaging element
29 bending operation knob
30 air/water supply button
31 suction button
32 still image pick-up command unit
33 treatment tool introduction port
35 light guide
36 signal cable
37a connector
37b connector
38 moving image
38a frame image
39 still image
40 time-series image acquiring unit
41 region-of-interest detecting unit
42 region-of-interest information acquiring unit
43 coordinates calculating unit
44 total-time measuring unit
45 emphasis-degree setting unit
46 identical-region-of-interest determining unit
47 control unit
48 display control unit
48A image display control unit
48B reporting information display control unit
49 storage unit
50 region-of-interest storage unit
51 program
D1, D2 data
E1 to E113 figure
R1 to R13 region of interest
S1 to S22 step of medical image processing method

What is claimed is:

1. A medical image processing apparatus comprising a processor configured to:
   acquire a plurality of medical images including a first medical image and a second medical image preceding the first medical image in time-series;
   display the medical images in time-series;
   emphasize regions of interest included in the medical images at set emphasis degrees; and
   determine whether a first region of interest included in the first medical image is identical with a second region of interest included in the second medical image,
   wherein the processor is configured to, in a case where the processor determines that the first region of interest is identical with the second region of interest, set one of the emphasis degrees for the first region of interest to a relatively larger value than another of the emphasis degrees which is set preceding the one of the emphasis degrees in time-series.

2. The medical image processing apparatus according to claim 1, wherein the processor is further configured to:
   measure a second total time during which the second region of interest is detected or emphasized;

in the case where the processor determines that the first region of interest is identical with the second region of interest, measure a first total time during which the first region of interest is detected or emphasized by taking over the second total time;
in a case where the processor determines that the first region of interest is not identical with the second region of interest, measure the first total time independently of the second total time; and
set the one of the emphasis degrees to a relatively larger value as the first total time is relatively longer.

3. The medical image processing apparatus according to claim 1, wherein the processor is further configured to:
in the case where the first region of interest is not identical with the second region of interest, determine whether the first region of interest is identical with a third region of interest included in a third medical image preceding the second medical image in time-series;
measure a third total time during which the third region of interest is detected or emphasized;
in the case where the first region of interest is identical with the third region of interest, measure a first total time during which the first region of interest is detected or emphasized by taking over the third total time;
in the case where the first region of interest is not identical with the third region of interest, measure the first total time independently of the third total time; and
set the one of the emphasis degrees to a relatively larger value as the first total time is relatively longer.

4. The medical image processing apparatus according to claim 1, wherein the processor is configured to determine whether the first region of interest is identical with the second region of interest according to a similarity degree or a positional difference between the first region of interest and the second region of interest.

5. The medical image processing apparatus according to claim 2, wherein the processor is further configured to:
superpose a figure indicating a position of the first region of interest on the first medical image; and
set a transmittance of the figure to a relatively lower transmittance as the first total time is relatively longer.

6. The medical image processing apparatus according to claim 2, wherein the processor is further configured to:
superpose a figure indicating a position of the first region of interest on the first medical image; and
set a color of the figure to a relatively higher color intensity based on a color intensity index as the first total time is relatively longer.

7. The medical image processing apparatus according to claim 2, wherein the processor is further configured to:
superpose a figure indicating a position of the first region of interest on the first medical image; and
set a size of the figure to a relatively larger size as the first total time is relatively longer.

8. The medical image processing apparatus according to claim 2, wherein the processor is further configured to:
superpose a frame-shaped figure surrounding the first region of interest on the first medical image; and
set a line thickness of the frame-shaped figure to be relatively thicker as the first total time is relatively longer.

9. The medical image processing apparatus according to claim 2, wherein the processor is further configured to increase at least one of a minimum of the emphasis degree, a maximum of the emphasis degree, or an increasing rate of the emphasis degree to the total time, as a number of regions of interest existing in each medical image relatively increases.

10. The medical image processing apparatus according to claim 2, wherein the processor is further configured to change at least one of a minimum of the one of the emphasis degrees, a maximum of the one of the emphasis degrees, or an increasing rate of the one of the emphasis degrees to the first total time, according to a position of the first region of interest in the first medical image.

11. The medical image processing apparatus according to claim 2, wherein the processor is further configured to change at least one of a minimum of the one of the emphasis degrees, a maximum of the one of the emphasis degrees, or an increasing rate of the one of the emphasis degrees to the first total time, according to luminance of the first region of interest or a difference between the luminance of the first region of interest and luminance of a region outside the first region of interest.

12. The medical image processing apparatus according to claim 2, wherein the processor is further configured to change at least one of a minimum of the one of the emphasis degrees, a maximum of the one of the emphasis degrees, or an increasing rate of the one of the emphasis degrees to the first total time, according to color information of the first region of interest or a difference between the color information of the first region of interest and color information of a region outside the first region of interest.

13. The medical image processing apparatus according to claim 2, wherein the processor is further configured to change at least one of a minimum of the one of the emphasis degrees, a maximum of the one of the emphasis degrees, or an increasing rate of the one of the emphasis degrees to the first total time, according to a movement amount of the first region of interest or a movement direction of the first region of interest.

14. The medical image processing apparatus according to claim 1, wherein the medical images are endoscopic images, capsule-endoscopic images or ultrasound images.

15. The medical image processing apparatus according to claim 1, wherein the processor is further configured to cause a display to display the first medical image in which the first region of interest is emphasized.

16. The medical image processing apparatus according to claim 1, wherein the processor is further configured to cause at least one of displays to display the first medical image in which the first region of interest is emphasized.

17. The medical image processing apparatus according to claim 1, wherein the processor is further configured to sequentially display each of the medical images.

18. A diagnosis supporting apparatus comprising:
the medical image processing apparatus according to claim 15; and
the display.

19. An endoscope system comprising:
the medical image processing apparatus according to claim 1; and
an endoscope configured to capture the medical images.

20. An operating method of a medical image processing apparatus, the method comprising:
acquiring a plurality of medical images including a first medical image and a second medical image preceding the first medical image in time-series;
displaying the medical images in time-series;
emphasizing regions of interest included in the medical images at set emphasis degrees;

determining whether a first region of interest included in the first medical image is identical with a second region of interest included in the second medical image; and setting one of the emphasis degrees for the first region of interest in a case where the first region of interest is identical with the second region of interest to a relatively larger value than another of the emphasis degrees which is set preceding the one of the emphasis degrees.

21. An operating method of an endoscope system comprising a medical image processing apparatus and an endoscope configured to capture a plurality of medical images, the method comprising:

acquiring the medical images including a first medical image and a second medical image preceding the first medical image in time-series;

displaying the medical images in time-series;

emphasizing regions of interest included in the medical images at a set emphasis degree;

determining whether a first region of interest included in the first medical image is identical with a second region of interest included in the second medical image; and setting one of the emphasis degrees for the first region of interest in a case where the first region of interest is identical with the second region of interest to a relatively larger value than another of the emphasis degrees which is set preceding the one of the emphasis degrees.

22. A non-transitory computer-readable recording medium causing a computer to execute the method according to claim 21 upon the computer reading a command stored in the recording medium.

23. A non-transitory computer-readable recording medium causing a computer to execute the method according to claim 22 upon the computer reading a command stored in the recording medium.

* * * * *